US012178820B2

(12) United States Patent
Dietrich et al.

(10) Patent No.: US 12,178,820 B2
(45) Date of Patent: *Dec. 31, 2024

(54) COMPOSITIONS AND METHODS FOR THEIR PRODUCTION

(71) Applicant: RAREBIRD, INC., San Francisco, CA (US)

(72) Inventors: Jeffrey Dietrich, San Francisco, CA (US); Maddison Kylie Gurrola, San Francisco, CA (US); Amanda Jacklyn Grace Sinrod, San Francisco, CA (US); Edwin Yparraguirre Palang, San Mateo, CA (US)

(73) Assignee: RAREBIRD, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/412,318

(22) Filed: Jan. 12, 2024

(65) Prior Publication Data

US 2024/0189314 A1 Jun. 13, 2024

Related U.S. Application Data

(63) Continuation of application No. 18/299,323, filed on Apr. 12, 2023, now Pat. No. 11,872,232, which is a continuation of application No. PCT/US2022/026849, filed on Apr. 28, 2022.

(60) Provisional application No. 63/181,915, filed on Apr. 29, 2021.

(51) Int. Cl.
| | |
|---|---|
| *A61K 31/522* | (2006.01) |
| *A23F 5/20* | (2006.01) |
| *A61K 9/14* | (2006.01) |
| *A61K 36/74* | (2006.01) |

(52) U.S. Cl.
CPC .............. *A61K 31/522* (2013.01); *A23F 5/20* (2013.01); *A61K 9/14* (2013.01); *A61K 36/74* (2013.01)

(58) Field of Classification Search
CPC ................................. A23F 5/20; A61K 31/522
See application file for complete search history.

(56) References Cited

U.S. PATENT DOCUMENTS

| | | | |
|---|---|---|---|
| 5,208,056 | A | 5/1993 | Fischer et al. |
| 5,455,057 | A | 10/1995 | Symbolik et al. |
| 6,734,342 | B2 | 5/2004 | Sano et al. |
| 2007/0009574 | A1 | 1/2007 | Decombaz et al. |
| 2009/0325984 | A1 | 12/2009 | Costentin et al. |
| 2011/0086138 | A1 | 4/2011 | Jia et al. |
| 2011/0318474 | A1 | 12/2011 | Berry et al. |
| 2012/0258202 | A1 | 10/2012 | Cairns |
| 2016/0120201 | A9 | 5/2016 | Kelly et al. |
| 2023/0072854 | A1* | 3/2023 | Purpura ............... A61K 21/522 |

FOREIGN PATENT DOCUMENTS

| | | |
|---|---|---|
| WO | 98007330 A1 | 2/1998 |
| WO | 2021151094 A1 | 7/2021 |
| WO | 2022056190 A2 | 3/2022 |
| WO | 2022204180 A1 | 9/2022 |
| WO | 2022204598 A1 | 9/2022 |
| WO | 2022212770 A1 | 10/2022 |
| WO | 2022217000 A1 | 10/2022 |
| WO | 2022232469 A1 | 11/2022 |
| WO | 2023009655 A1 | 2/2023 |
| WO | 2023009681 A1 | 2/2023 |

OTHER PUBLICATIONS

Sandra K. Szlapinski et al, Paraxanthine safety and comparison to caffeine, Frontiers in Toxicology, vol. 5, Year: 2023 (Year: 2023).*
Meredith B Mock et al, Biocatalytic Production and Purification of the High-value Biochemical Paraxanthine, Biotechnology and Bioprocess Engineering 27: 640-651, 2022 (Year: 2022).*
Barista.com (Fresh Roasted Coffee LLC . . . experiences? Message board, Mar. 7, 2015 post by EspressoForge) (Year: 2015).*
Awwad et al, Quantification of Caffeine and Chlorogenic Acid in Green and Roasted Coffee Samples Using HPLC-DAD and Evaluation of the Effect of Degree of Roasting on Their Levels. Molecules. Dec. 11, 2021;26(24):7502.
Cayman, Product Information, Paraxanthine, Item No. 21068, 2022 (1 page).
Committee on Military Nutrition Research, Food and Nutrition Board, Institute of Medicine, "Caffeine for the Sustainment of Mental Task Performance: Formulations for Military Operations", ISBN: 0-309-56594-4, 172 pages, (2001); retrieved from http://www.nap.edu/catalog/10219.html.
Nonappa and Kolehmainen, Caffeine as a Gelator. Gels. Mar. 2, 2016;2(1):9 (10 pages).
Okura et al., Effects of Paraxanthine and Caffeine on Sleep, Locomotor Activity, and Body Temperature in Orexin/Ataxin-3 Transgenic Narcoleptic Mice. Sleep. Jul. 2010;33(7):930-942.
Thorn et al, PharmGKB summary: caffeine pathway. Pharmacogenet Genomics. May 2012;22(5):389-395.
Xing et al., Dose-Response of Paraxanthine on Cognitive Function: A Double Blind, Placebo Controlled, Crossover Trial. Nutrients. Dec. 15, 2021;13(12):4478 (14 pages).

(Continued)

*Primary Examiner* — Mark V Stevens
*Assistant Examiner* — Alparslan Asan
(74) *Attorney, Agent, or Firm* — Michael A. Whittaker

(57) ABSTRACT

Provided herein include caffeinated, partially decaffeinated, and decaffeinated paraxanthine beverages, coffees and paraxanthine coffee beverages. Also provided are methods for the production of caffeinated, partially decaffeinated, and decaffeinated paraxanthine beverages, coffees and paraxanthine coffee beverages. In some embodiments, disclosed compositions may provide consumers with increased alertness and wakefulness, while preventing side effects commonly associated with caffeinated drinks.

18 Claims, 1 Drawing Sheet

(56) References Cited

OTHER PUBLICATIONS

International Search Report and Written Opinion issued in PCT/US2022/026849 dated Jul. 29, 2022 (12 pages).

* cited by examiner

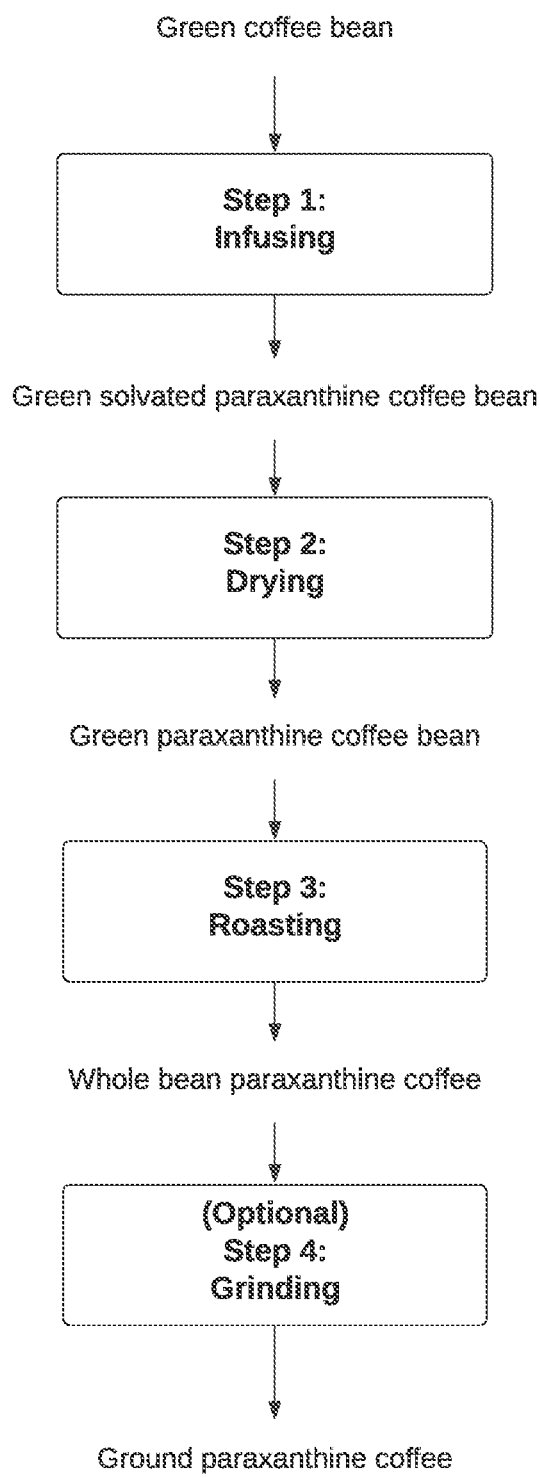

COMPOSITIONS AND METHODS FOR THEIR PRODUCTION

CROSS-REFERENCE TO RELATED APPLICATIONS

The present application is a continuation of U.S. patent application Ser. No. 18/299,323, filed on Apr. 12, 2023, now U.S. Pat. No. 11,872,232, which is a continuation of International Patent Application No. PCT/US2022/026849, filed on Apr. 28, 2022, which claims the benefit of U.S. provisional application Ser. No. 63/181,915, filed on Apr. 29, 2021, each of which is incorporated herein in its entirety.

FIELD

Consumable compositions such as beverages are provided herein as well as methods of their production. In some embodiments caffeinated, partially decaffeinated, and decaffeinated beverages and/or coffee comprising paraxanthine, salts thereof and/or hydrates thereof are disclosed.

BACKGROUND

Caffeine, an adenosine A1 and A2a receptor antagonist, is a widely used stimulant for its wakefulness promoting properties. However, some consumers may find one dose of caffeine not to be strong enough, and/or repetitive caffeine consumption may bring about undesirable side effects, such as anxiety, irritability, tremors, jitteriness and increased urination.

Therefore, a need exists for caffeine-free and caffeine-reduced coffees and energy drinks with high wakefulness properties that are suitable for consumption, and can consistently cause stimulating effects without exacerbating anxiety and irritability.

SUMMARY

In various aspects and embodiments present disclosure includes paraxanthine compositions (such as coffee and energy beverages), methods to produce such paraxanthine coffees and beverages, and paraxanthine drinks produced by said methods.

The term "paraxanthine" as used herein refers to a chemical having the following formula (or a salt thereof or a hydrate thereof): $C_7H_8N_4O_2$, with Chemical Abstracts Service (CAS) number: 611-59-6.

Thus, in one aspect, provided herein are paraxanthine compositions. As used herein a "paraxanthine composition" is a liquid or solid composition that includes paraxanthine or a salt thereof or a hydrate thereof. In some embodiments a paraxanthine composition is suitable for consumption by an animal or human. In some embodiments, a paraxanthine composition of the disclosure is a paraxanthine coffee and/or paraxanthine beverage. In certain embodiments, a paraxanthine composition of the disclosure increases alertness, wakefulness, and productivity upon consumption, and in some embodiments without increasing anxiety, jitteriness, and irritability (or causing less of an increase in anxiety, jitteriness, and irritability as compared to a comparable caffeinated composition). In various embodiments, the disclosed paraxanthine compositions comprise from about 0.005% (w/w) and 10% (w/w), or between 0.005% (w/w) and 9% (w/w), or between 0.005% (w/w) and 8% (w/w), or between 0.005% (w/w) and 7% (w/w), or between 0.005% (w/w) and 6% (w/w), or between 0.005% (w/w) and 5% (w/w), or between 0.005% (w/w) and 4% (w/w), or between 0.005% (w/w) and 3% (w/w), or between 0.005% (w/w) and 2% (w/w), or between 0.05% (w/w) and 10% (w/w), or between 0.05% (w/w) and 9% (w/w), or between 0.05% (w/w) and 8% (w/w), or between 0.05% (w/w) and 7% (w/w), or between 0.05% (w/w) and 6% (w/w), or between 0.05% (w/w) and 5% (w/w), or between 0.05% (w/w) and 4% (w/w), or between 0.05% (w/w) and 3% (w/w), or between 0.05% (w/w) and 2% (w/w), or between 0.5% (w/w) and 10% (w/w), or between 0.5% (w/w) and 9% (w/w), or between 0.5% (w/w) and 8% (w/w), or between 0.5% (w/w) and 7% (w/w), or between 0.5% (w/w) and 6% (w/w), or between 0.5% (w/w) and 5% (w/w), or between 0.5% (w/w) and 4% (w/w), or between 0.5% (w/w) and 3% (w/w), or between 0.5% (w/w) and 2% (w/w), or about 0.005% (w/w), or about 0.01% (w/w), or about 0.02% (w/w), or about 0.03% (w/w), or about 0.05% (w/w), or about 0.075% (w/w), or about 0.10% (w/w), or about 0.250% (w/w), or about 0.50% (w/w), or about 0.6% (w/w), or about 0.7% (w/w), or about 0.8% (w/w), or about 0.9% (w/w), or about 1.10% (w/w), or about 1.2% (w/w), or about 1.2% (w/w), or about 1.25% (w/w), or about 1.3% (w/w), or about 1.4% (w/w), or about 1.5% (w/w), or about 1.6% (w/w), or about 1.7% (w/w), or about 1.8% (w/w), or about 1.9% (w/w), or about 2% (w/w), or about 2.25% (w/w), or about 2.5% (w/w) paraxanthine.

As used herein, the term "coffee" means the seed of a plant of genus *Coffea*, including *Coffea arabica* and *Coffea robusta* species, as well as extracts produced from said seed, or other compositions (liquid or solid compositions) that includes coffee seed, or parts or extracts thereof. A "paraxanthine coffee" as used herein is coffee that is a paraxanthine composition as provided herein. When referring to coffee in the seed form, said seed may be the whole seed or a part of the seed; the seed may be unroasted or roasted. When referring to coffee as an extract of a seed, said extract may be derived from an unroasted coffee seed or a roasted coffee seed. The terms "bean" and "seed" as refers to coffee are used interchangeably in the disclosure. A coffee bean of the disclosure may be a ground or unground coffee bean. As used herein, "whole bean coffee bean", "whole bean", or "unground coffee bean" refers to coffee beans having a particle size greater than 1.5 mm; "ground coffee" or "ground coffee bean" refers to coffee beans having a particle size of less than 1.5 mm. A coffee bean or ground coffee bean of the disclosure may be roasted or unroasted. As used herein, the term "coffee beverage" is a liquid composition suitable for consumption that includes coffee. In some embodiments a coffee beverage is obtained by extracting or brewing a coffee bean (such as, for example, a ground coffee bean; a roasted coffee bean; or a ground roasted coffee bean). A "paraxanthine coffee beverage" as used herein is coffee beverage that is a paraxanthine composition as provided herein. In some embodiments a coffee beverage as used herein is produced from the brewing extracting of a paraxanthine coffee bean or from the brewing or extraction of a decaffeinated coffee bean followed by the addition of paraxanthine.

In some embodiments, the disclosed paraxanthine coffees are in form of whole roasted coffee beans or ground roasted coffee beans. The whole or ground roasted coffee beans may comprise about 0.05% (w/w), 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2.0% (w/w), 2.1% (w/w), 2.2% (w/w), 2.3% (w/w), 2.4% (w/w), 2.5%

(w/w), 2.6% (w/w), 2.7% (w/w), 2.8% (w/w), 0.7% (w/w), 2.9% (w/w), 3.0% (w/w), 3.1% (w/w), 3.2% (w/w), 3.3% (w/w), 3.4% (w/w), 3.5% (w/w), 3.6% (w/w), 3.7% (w/w), 3.8% (w/w), or about 3.9% (w/w) paraxanthine, a salt thereof or a hydrate thereof. In various embodiments, the whole or ground roasted coffee beans may comprise between 0.05% (w/w) and 10% (w/w), or between 0.05% (w/w) and 9% (w/w), or between 0.05% (w/w) and 8% (w/w), or between 0.05% (w/w) and 7% (w/w), or between 0.05% (w/w) and 6% (w/w), or between 0.05% (w/w) and 5% (w/w), or between 0.05% (w/w) and 4% (w/w), or between 0.05% (w/w) and 3% (w/w), or between 0.05% (w/w) and 2% (w/w), or between 0.5% (w/w) and 10% (w/w), or between 0.5% (w/w) and 9% (w/w), or between 0.5% (w/w) and 8% (w/w), or between 0.5% (w/w) and 7% (w/w), or between 0.5% (w/w) and 6% (w/w), or between 0.5% (w/w) and 5% (w/w), or between 0.5% (w/w) and 4% (w/w), or between 0.5% (w/w) and 3% (w/w), or between 0.5% (w/w) and 2% (w/w) paraxanthine.

The term "decaffeinated" as used herein with respect to coffee beans, means the majority of caffeine naturally present in a green coffee bean has been removed. In some embodiments, decaffeinated means at least 90%; 91%; 92%; 93%; 94%; 95%; 96%; 97%; 98%; 99%; or more of the caffeine naturally present in a corresponding green coffee bean has been removed. In some embodiments, decaffeinated means a composition (such as a beverage, coffee beverage, coffee bean, etc.) that comprises less than less than 0.3% (w/w), less than 0.25% (w/w), less than 0.2% (w/w), less than 0.15% (w/w), less than 0.1% (w/w), less than 0.05% (w/w), less than 0.01% (w/w), or less than 0.005% (w/w) caffeine. In certain embodiments, decaffeinated means a composition (such as a beverage, coffee beverage, coffee bean, etc.) that comprises an undetectable amount of caffeine (i.e., 0% w/w caffeine content) using standard caffeine detection and analysis methods known in the art. The term "partially decaffeinated" as used herein with regard to a coffee bean means a composition having a caffeine content less than that of a normal coffee or coffee bean, yet wherein some caffeine remains. In some embodiments a partially decaffeinated composition with respect to a solid composition, such as, for example a coffee bean, has between 0.20% (w/w) and 0.80% (w/w), or between 0.3% (w/w) and 0.70% (w/w), or between 0.40% (w/w) and 0.6% (w/w). In some embodiments a partially decaffeinated composition with respect to a liquid composition for consumption (such as a paraxanthine beverage), such as, for example a coffee beverage, a beverage, an energy drink, etc., has between 0.005% (w/w) and 0.15% (w/w). In some embodiments, the disclosed paraxanthine coffees are decaffeinated or partially decaffeinated paraxanthine coffees.

In some embodiments, the disclosed paraxanthine coffees are paraxanthine beverages. Suitable paraxanthine beverages include, but are not limited to, brewed paraxanthine coffees, espresso paraxanthine coffees, instant paraxanthine coffees, ready-to-drink paraxanthine coffee beverages, roasted paraxanthine coffee beverages, paraxanthine milk shakes, paraxanthine energy drinks, paraxanthine sodas, paraxanthine diet drinks, paraxanthine supplement drinks, and paraxanthine sport beverages.

In some embodiments, the disclosed paraxanthine beverages are decaffeinated or partially decaffeinated paraxanthine beverages as provided herein.

In some embodiments, the disclosed paraxanthine coffee beverages are brewed paraxanthine coffees. The brewed paraxanthine coffees may comprise from about 200 to about 1,000 mg paraxanthine, a salt thereof or a hydrate thereof/liter.

In other embodiments, the disclosed paraxanthine coffee beverages are espresso paraxanthine coffees. The espresso paraxanthine coffees may comprise from about 1,000 to about 2,500 mg paraxanthine, a salt thereof or a hydrate thereof/liter.

In some embodiments, the disclosed paraxanthine beverages may comprise from about 50 to about 200 mg paraxanthine, a salt thereof or a hydrate thereof/serving.

Additionally, provided herein are methods of producing the disclosed paraxanthine coffee, and paraxanthine coffee produced by such methods. The disclosed methods comprise adding paraxanthine, a salt thereof or a hydrate thereof, to coffee beans by solid-solid grinding, paraxanthine absorption, or paraxanthine adsorption.

In some embodiments, the disclosed methods may further comprise decaffeinating or partially decaffeinating the coffee beans prior to, or contemporaneous to, adding paraxanthine, a salt thereof or a hydrate thereof, by extracting caffeine from the coffee beans into a solvent selected from water, ethyl acetate, methylene chloride, supercritical carbon dioxide, and subcritical carbon dioxide.

In some embodiments, solid-solid grinding may comprise (i) grinding from about 10% (w/w) to about 30% (w/w) paraxanthine, a salt thereof or a hydrate thereof into roasted, decaffeinated coffee beans; (ii) forming a stable, evenly-colored paraxanthine-decaffeinated coffee mixture by compression and friction; and (iii) adding additional ground decaffeinated coffee to obtain a paraxanthine coffee comprising from about 0.5% (w/w) to about 4% (w/w) paraxanthine, a salt thereof or a hydrate thereof.

Solid-solid grinding may be performed by one or more techniques, such as mortar and pestle, ball mill, rod mill, and vertical roller mills.

In some embodiments, paraxanthine, a salt thereof or a hydrate thereof, is added to the coffee beans by absorption. In some embodiments, absorption may comprise steeping unroasted coffee beans in an aqueous solution comprising from about 1 g/l to about 300 g/l paraxanthine, a salt thereof or a hydrate thereof, at a temperature between 25° C. and 100° C., to allow diffusion and absorption of paraxanthine into the unroasted coffee beans. In other embodiments, absorption may comprise steeping unroasted coffee beans in an infusion solvent selected from the group consisting of ethyl acetate, ethanol, methylene chloride, supercritical carbon dioxide, and isopropanol wherein said infusion solvent comprises between about 1 g/l to about 300 g/l paraxanthine, a salt thereof or a hydrate thereof.

In some embodiments, the unroasted coffee beans are decaffeinated unroasted coffee beans. In other embodiments, the unroasted coffee beans are decaffeinated during paraxanthine diffusion and absorption.

In some embodiments, paraxanthine, a salt thereof or a hydrate thereof, is added to the coffee beans by adsorption. Adsorption may comprise coating a paraxanthine solution comprising from about 10 g/l to about 300 g/l paraxanthine, a salt thereof or a hydrate thereof, onto unroasted decaffeinated coffee beans by spraying or by rotating drum mixer. The paraxanthine, a salt thereof or a hydrate thereof may be dissolved in water, ethyl acetate, methylene chloride, supercritical carbon dioxide, or subcritical carbon dioxide.

Also provided herein is a process of preparing a paraxanthine coffee beverage that increases alertness, wakefulness, and productivity upon consumption, without increasing anxiety, jitteriness, and irritability. The disclosed paraxanthine coffee beverage may comprise from about 0.5% (w/w) to about 4% (w/w) paraxanthine, a salt thereof or a hydrate thereof. The disclosed process comprises adding paraxanthine, a salt thereof or a hydrate thereof, to coffee beans by solid-solid grinding, paraxanthine absorption, or paraxanthine adsorption.

In some embodiments, solid-solid grinding comprises: (i) grinding from about 10% (w/w) to about 30% (w/w) paraxanthine, a salt thereof or a hydrate thereof into roasted coffee beans; (ii) forming a stable, evenly-colored paraxanthine coffee mixture by compression and friction; and (iii) adding additional ground coffee to obtain a paraxanthine coffee comprising from about 0.5% (w/w) to about 4% (w/w) paraxanthine, a salt thereof or a hydrate thereof.

In some embodiments, absorption may comprise steeping unroasted coffee beans in an aqueous solution comprising from about 1 g/l to about 300 g/l paraxanthine, a salt thereof or a hydrate thereof, at a temperature between 25° C. and 100° C., to allow diffusion and absorption of paraxanthine into the unroasted coffee beans. In other embodiments, absorption may comprise steeping unroasted coffee beans in an infusion solvent selected from the group consisting of ethyl acetate, ethanol, methylene chloride, supercritical carbon dioxide, and isopropanol wherein said infusion solvent comprises between about 1 g/l to about 300 g/l paraxanthine, a salt thereof or a hydrate thereof.

In some embodiments, adsorption may comprise coating a paraxanthine solution comprising from about 10 g/l to about 300 g/l paraxanthine, a salt thereof or a hydrate thereof, in water, ethyl acetate, methylene chloride, supercritical carbon dioxide, or subcritical carbon dioxide, onto unroasted coffee beans.

In some embodiments, the disclosed process may further comprise decaffeinating or partially decaffeinating the coffee beans prior to or while adding to, steeping into, or coating paraxanthine, a salt thereof or a hydrate thereof, onto unroasted coffee beans, by extracting caffeine from the coffee beans into a solvent selected from water, ethyl acetate, methylene chloride, supercritical carbon dioxide, and subcritical carbon dioxide.

Also provided herein is a paraxanthine coffee beverage produced by the processes described above.

Additionally provided herein is a method for increasing alertness, wakefulness, and productivity in a subject, without increasing anxiety, jitteriness, and irritability, wherein the method comprises administering to the subject the disclosed paraxanthine coffee beverages.

Suitable paraxanthine coffee beverages include, but are not limited to, brewed paraxanthine coffees, espresso paraxanthine coffees, paraxanthine coffee drinks, instant paraxanthine coffees, ready-to-drink paraxanthine coffee beverages, roasted paraxanthine coffee beverages.

The paraxanthine coffees and paraxanthine coffee beverages provided herein in some embodiments present several attractive features and desirable properties that may make them suitable for consumption several times a day, and at any time of day or night. For example, paraxanthine may provide the consumer with a higher level of alertness, wakefulness, and productivity compared to caffeine, while it prevents or reduces undesirable side effects associated with caffeine consumption, such as increased levels of anxiety, jitteriness, and irritability. Therefore, the disclosed paraxanthine coffees and paraxanthine coffee beverages in some embodiments increase the ability to focus and prevent aggressive behavior.

In addition, paraxanthine may have a reduced level of toxicity compared to caffeine. Thus, the disclosed paraxanthine coffees and paraxanthine coffee beverages in some embodiments are safe and caffeine-dependency free.

The foregoing and other features of the disclosure will become more apparent from the following detailed description of several embodiments.

BRIEF DESCRIPTION OF THE DRAWINGS

FIG. 1 is a block flow of infusion method used to convert green coffee beans to whole bean paraxanthine coffee and ground paraxanthine coffee.

DETAILED DESCRIPTION OF THE INVENTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

To facilitate review of the various embodiments of this disclosure, the following explanations of specific terms are provided:

Absorption: A process by which a first substance diffuses or it is taken up into the structure of a second substance. For example, by paraxanthine absorption into coffee beans, it is meant that paraxanthine is taken up and absorbed into the structure of the coffee beans.

Active Ingredient: A biologically active ingredient in a finished product having a direct effect in restoring, correcting or modifying one or more physiological functions in a subject, such as a human or animal subject.

Adsorption: A process by which a first substance forms a thin film on the surface of a second substance. For example, by paraxanthine adsorption into coffee beans, it is meant that paraxanthine is adsorbed onto the coffee beans and it forms a thin layer on the surface of the coffee beans.

Analog: A compound having a structure similar to another, but differing from it, for example, in one or more atoms, functional groups, or substructure. Active ingredient analogs encompass compounds that are structurally related to naturally occurring active ingredients, but whose chemical and biological properties may differ from naturally occurring active ingredients, as well as compounds derived from a naturally occurring active ingredient by chemical, biological or a semi-synthetic transformation.

Administer: To provide or give a subject a composition by an effective route. Application is local. Exemplary routes of application include, but are not limited to, oral routes.

Antioxidant: An active agent that inhibits oxidation or reactions promoted by oxygen or peroxides.

Contacting: Placement in direct physical association; includes both in solid and liquid form.

Control: A reference standard. In some examples, a control is a known value or range of values, such as one indicative of the presence or the absence of a disease. In some examples, a control is a value or range of values, indicating a response in the absence of a therapeutic agent.

Effective amount: The amount of an active agent (alone or with one or more other active agents) sufficient to induce a desired response, such as to prevent, treat, reduce and/or ameliorate a condition.

Emulsifier: A surfactant that reduces the interfacial tension between oil and water, minimizing the surface energy through formation of globules. Emulsifiers include gums, fatty acid conjugates and cationic, anionic and amphoteric surfactants capable of suspending the oily phase and stabilizing the emulsion by coating the oil droplets and avoiding the separation of the internal oily phase. The film coat produced by the emulsifier is a barrier between the immiscible phase and it also prevents droplets association, coagulation and coalescence. Examples of emulsifier include, but are not limited to, lecithin, glyceryl monostearate, methylcellulose, sodium lauryl sulfate, sodium oleate, sorbitan monopalmitate, sorbitan monostearate, sorbitan tristrearate, tragacanth, triethanolamine oleate, polyethylene sorbitan monolaurate, poloxamer, detergents, Tween 80 (polyoxyethylene sorbitan monooleate), Tween 20 (polyoxyethylene sorbitan monolaurate), cetearyl glucoside, polyglucosides, sorbitan monooleate (Span 80), sorbitan monolaurate (Span 20), polyoxyethylene monostearate (Myrj 45), polyoxyethylene vegetable oil (Emulphor), cetyl piridinium chloride, polysaccharides gums, Xanthan gums, Tragacanth, Gum *arabica*, Acacia, or proteins and conjugated proteins capable of forming and protecting stable oil in glycerin emulsion.

Green paraxanthine coffee beans: whole green coffee beans (i.e., unroasted) that comprise paraxanthine in an amount greater than 0.05% (w/w) and have a moisture content less than 12.5% w/w.

Hydrophilic: A polymer, substance or compound that is capable of absorbing more than 10% of water at 100% relative humidity (RH).

Hydrophobic: A polymer, substance or compound that is capable of absorbing no more than 1% of water at 100% relative humidity (RH).

Lipophilic: A substance or compound that has an affinity for a non-polar environment compared to a polar or aqueous environment.

Oral administration: Delivery of an active agent through the mouth.

Organoleptic: A property of an edible substance or liquid that an individual experiences via the senses, including taste, sight, smell, and touch.

Paraxanthine: A compound having the chemical formula $C_7H_8N_4O_2$ and corresponding to CAS number 611-59-6, as well as its salts (non-limiting examples of which include magnesium paraxanthine, calcium paraxanthine, sodium paraxanthine, and potassium paraxanthine), its hydrates, as well as hydrated paraxanthine salts.

pH Adjuster or Modifier: A molecule or buffer used to achieve desired pH control in a formulation. Exemplary pH modifiers include acids (e.g., acetic acid, adipic acid, carbonic acid, citric acid, fumaric acid, phosphoric acid, sorbic acid, succinic acid, tartaric acid, basic pH modifiers (e.g., magnesium oxide, tribasic potassium phosphate), and pharmaceutically acceptable salts thereof.

Purification: Any technique or method that increases the degree of purity of a substance of interest, such as an enzyme, a protein, or a compound, from a sample comprising the substance of interest. Non-limiting examples of purification methods include silica gel column chromatography, size exclusion chromatography, hydrophobic interaction chromatography, ion exchange chromatography including, but not limited to, cation and anion exchange chromatography, free-flow-electrophoresis, high performance liquid chromatography (HPLC), and differential precipitation.

Subject: A living multi-cellular vertebrate organism, such as a human and a non-human mammal.

Supercritical Fluid: Any substance at a temperature and pressure above their critical point, where distinct liquid and gas phases do not exist. Solubility of a material in the fluid increases as the density of the fluid increases. Density of the fluid increases with pressure, and at constant density, solubility of a material in the fluid increases as the temperature increases. Exemplary supercritical fluids include, but are not limited to, carbon dioxide, water, methane, propane, ethane, ethylene, propylene, methanol, ethanol, acetone and nitrogen oxide.

Paraxanthine Coffees, Paraxanthine Coffee Beverages, and Production Methods Thereof Caffeinated and decaffeinated coffees and coffee beverages are extremely popular. However, caffeinated coffees and coffee beverages cause many consumers to experience undesirable side effects, such as anxiety, jitteriness, irritability, nervousness, and tremors. Most coffee beans comprise from about 0.5% (w/w) to about 2.5% (w/w) of caffeine. Decaffeinated coffees and decaffeinated coffee beverages have been developed to address many of the downsides of caffeinated drinks. However, caffeine content in decaffeinated drinks is not strictly regulated in the United States. The United States Food and Drug Administration (FDA) requires the removal of 97% of the initial caffeine content from coffee beans for the production of decaffeinated coffee. However, the FDA does not have rules on the initial caffeine content. Decaffeinated coffee in the United States typically comprises from about 0.015% (w/w) to about 0.075% (w/w) of caffeine, and many consumers experience some of the side effects associated with caffeine after consuming decaffeinated drinks. Accordingly, there is a need for caffeine alternatives, that provide the desired benefits of caffeine with none of or, at least, fewer negative side effects associated with caffeine consumption.

The present application satisfies this need, by providing paraxanthine coffees, paraxanthine coffee beverages, and methods for their production.

Paraxanthine is the primary metabolite of caffeine in humans, and about 80-85% of consumed caffeine is converted to paraxanthine in the liver. Because paraxanthine has a shorter half-life than caffeine (3.1±0.8 for paraxanthine, compared to 4.1±0.8 hours for caffeine), paraxanthine is cleared from the body faster than caffeine. Additionally, unlike caffeine, paraxanthine's metabolites are inactive and do not have stimulatory qualities. Thus, because of paraxanthine's shorter retention time in the body, the paraxanthine coffees and paraxanthine coffee beverages provided herein produce less anxiogenic effects than caffeinated and decaffeinated coffees, and, consequently, decrease aggressive behavior, improve mood and cognition, and reduce stress. In addition, the disclosed paraxanthine coffees and coffee beverages have less diuretic effects than caffeinated and decaffeinated coffees, and, unlike caffeine, do not cause cytotoxic and DNA damage.

Thus, the paraxanthine coffees and paraxanthine coffee beverages provided herein give consumers the desired benefits sought in regular coffee and energy drinks, without causing undesirable side effects associated with caffeinated drink consumption.

Suitable paraxanthine coffees, paraxanthine coffee beverages, and paraxanthine beverages according to the present disclosure include, but are not limited to, brewed paraxanthine coffees (including hot and cold brewed paraxanthine coffees), espresso paraxanthine coffees, paraxanthine coffee drinks, instant paraxanthine coffees, ready-to-drink paraxanthine coffee beverages, roasted paraxanthine coffee beverages, paraxanthine milk shakes, paraxanthine energy drinks, paraxanthine sodas, paraxanthine diet drinks, paraxanthine supplement drinks, and paraxanthine sport beverages.

In some embodiments, the disclosed paraxanthine coffees and paraxanthine coffee beverages are produced by adding paraxanthine to decaffeinated coffee beans. The decaffeinated coffee may be either wholly decaffeinated (i.e. containing a minimal amount of caffeine) or partially decaffeinated (i.e., containing a fraction of the caffeine found in the original coffee beans).

In some embodiments, paraxanthine salts and/or paraxanthine hydrates may be used in place of or in addition to anhydrous paraxanthine.

Paraxanthine salts may comprise protonated or negatively charged secondary amine groups at the 3N position. Suitable salts of paraxanthine include, but are not limited to, magnesium paraxanthine, calcium paraxanthine, sodium paraxanthine and potassium paraxanthine salts.

Paraxanthine hydrates are generated from paraxanthine or paraxanthine salt precipitation as solids from aqueous paraxanthine solutions which, when complexed with water, produce hydrates.

The decaffeinated coffee beans may be raw, or green, or it may roasted at the time the paraxanthine is added.

Paraxanthine Coffee

In one aspect, the present disclosure provides a paraxanthine coffee. In some embodiments, the paraxanthine coffee is a whole bean paraxanthine coffee. In other embodiments, the paraxanthine coffee is a ground paraxanthine coffee.

The present disclosure provides four aspects useful for helping to define paraxanthine coffee, namely, paraxanthine content, caffeine content, moisture content, and color. These four aspects apply to both whole bean and ground paraxanthine coffees.

Paraxanthine Content

A first aspect of paraxanthine coffee is the paraxanthine content. The paraxanthine content in paraxanthine coffees and paraxanthine coffee beverages may be expressed as the amount in weight of paraxanthine per amount in weight of paraxanthine coffee.

The amount of paraxanthine in the disclosed paraxanthine coffees and paraxanthine coffee beverages is an amount sufficient to provide the consumer with the desired positive effects upon brewing without the incidence of undesired, negative side effects, such as an amount in a range from about 0.5% w/w, or from about 50 mg paraxanthine per 10 grams paraxanthine roasted coffee, to about 4% w/w, or to about 400 mg paraxanthine per 10 grams paraxanthine roasted coffee.

In some instances, it may be preferable to blend a paraxanthine coffee with a paraxanthine content greater than 4% w/w with a roasted coffee comprising no paraxanthine or, at least, a lower paraxanthine content. This approach can be used to optimize the taste and paraxanthine content of the final coffee mixture. Thus, in some instances it is preferable to produce a paraxanthine coffee with a paraxanthine content greater than 4% w/w.

In some embodiments, the amount of paraxanthine in the disclosed paraxanthine coffee is between about 0.5% and about 10% w/w. In some embodiment, the amount of paraxanthine in the disclosed paraxanthine coffee may be between about 0.5% and 5% w/w. In some embodiments, the amount of paraxanthine in the disclosed paraxanthine coffees may be between about 0.5% and about 2.5% w/w. In some embodiments, the amount of paraxanthine in the disclosed paraxanthine coffee beverages may be between about 0.5% and about 1.5% w/w paraxanthine.

Thus, paraxanthine coffees provided by the present disclosure may comprise greater than 0.5% (w/w), 0.6% (w/w), 0.7% (w/w), 0.8% (w/w), 0.9% (w/w), 1.0% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2.0% (w/w), 2.1% (w/w), 2.2% (w/w), 2.3% (w/w), 2.4% (w/w), 2.5% (w/w), 2.6% (w/w), 2.7% (w/w), 2.8% (w/w), 0.7% (w/w), 2.9% (w/w), 3.0% (w/w), 3.1% (w/w), 3.2% (w/w), 3.3% (w/w), 3.4% (w/w), 3.5% (w/w), 3.6% (w/w), 3.7% (w/w), 3.8% (w/w), 3.9% (w/w), 4% (w/w), 4.1% (w/w), 4.2% (w/w), 4.3% (w/w), 4.4% (w/w), 4.5% (w/w), 4.6% (w/w), 4.7% (w/w), 4.8% (w/w), 4.9% (w/w), 5.0% (w/w), 6.0% (w/w), 7.0% (w/w), 8.0% (w/w), 9.0% (w/w) or about 10% (w/w) paraxanthine, a salt thereof or a hydrate thereof.

Espresso-style paraxanthine coffees and paraxanthine coffee beverages may contain a higher weight fraction of paraxanthine such as, for example, between about 1.5% w/w and about 2.5% w/w paraxanthine.

In some embodiments, the paraxanthine content in the disclosed paraxanthine coffees and paraxanthine coffee beverages is limited by a Generally Recognized As Safe (GRAS) notification or dossier. Thus, in some embodiments, according to the GRAS notification, the maximum allowable paraxanthine content in the disclosed paraxanthine coffees and paraxanthine coffee beverages is 0.5% w/w, 0.75% w/w, 1% w/w, 1.25% w/w, 1.5% w/w, 1.75% w/w, or greater than 1.75% w/w. In some embodiments, per a GRAS notification, the maximum allowable paraxanthine content is 1.05% w/w. In other embodiments, according to GRAS notification, the maximum allowable paraxanthine content in the disclosed paraxanthine coffees and paraxanthine coffee beverages is 1.5% w/w.

In addition to maximum allowable paraxanthine content, a GRAS notification may also limit the paraxanthine used to biologically-derived paraxanthine, or paraxanthine that is produced from naturally occurring raw materials, including, for example, naturally occurring caffeine. Biologically-derived paraxanthine (also referred to herein as biobased paraxanthine) can be distinguished from synthetic, or non-biologically-derived paraxanthine, by assessment of its C14 content (i.e. its biobased content). Using radiocarbon and isotope ratio mass spectrometry analysis, the C14 content of the paraxanthine can be measured. ASTM International has established a standard method (ASTM-D6866) for assessing biobased content by C14 measurement. In some embodiments, the paraxanthine coffee comprises paraxanthine with a biobased content of at least 85%. In many embodiments, the paraxanthine has a biobased content of 100%.

In additional embodiments, the paraxanthine content in the disclosed paraxanthine coffee beverages may be expressed as a weight of paraxanthine per volume fraction (e.g., mg/l) of paraxanthine coffee beverage, or as a weight of paraxanthine per serving fraction (e.g., mg/serving) of paraxanthine coffee beverage.

In some embodiments, where the paraxanthine coffee beverage is a brewed coffee, the paraxanthine content in the brewed coffee may be in a range from about between 200 mg/l to about 1,000 mg/l. In some embodiments, where the paraxanthine coffee beverage is an espresso coffee, the paraxanthine content in the espresso coffee may be in a range from about between 1,000 mg/l to about 2,500 mg/l.

In some embodiments, the paraxanthine content in the disclosed paraxanthine coffee beverages is in a range from about 50 mg/serving to about and 200 mg/serving. In some embodiments, the paraxanthine content in the disclosed paraxanthine coffee beverages is about 100 mg/serving.

Those skilled in the art will recognize that the paraxanthine content of the disclosed paraxanthine coffees can be readily measured by high-performance liquid chromatography (IPLC). In this analytical approach, paraxanthine from a known mass of paraxanthine coffee is extracted into water (or another suitable solvent) of know mass and the paraxanthine concentration measured by IPLC using a reference standard. The total amount of paraxanthine present in the coffee bean on a mass basis is then back calculated. Example 3 provides one HPLC analytical procedure suitable for determining both the paraxanthine and caffeine contents of the green coffee beans, paraxanthine coffees, and intermediates produced during practice of the methods of the present disclosure.

Caffeine Content

A second aspect of paraxanthine coffees and paraxanthine beverages (such as a coffee) is the caffeine content. The caffeine content in paraxanthine coffees, paraxanthine beverages, and paraxanthine coffee beverages may be expressed as the amount in weight of caffeine per amount in weight of paraxanthine coffee.

In some embodiments the caffeine content in the disclosed paraxanthine coffees and paraxanthine coffee beverages may be less than 2.5% w/w, or less than 1% w/w, or less than 0.25% w/w, or less than 0.1% w/w.

In other embodiments, where a higher content of caffeine is desirable, the caffeine content in the disclosed paraxanthine coffees and paraxanthine coffee beverages may be in a range from about 0.1% w/w to about 2.5% w/w; or about 0.25% w/w to about 1.5% w/w; or about 0.5% w/w to about 1% w/w.

In some embodiments, the disclosed paraxanthine coffee beverages may comprise less than 100 mg/l caffeine, less than 50 mg/l caffeine, or less than 25 mg/l caffeine. In some embodiments, the caffeine content in the disclosed paraxanthine coffee beverages is less than 25 mg/serving.

Example 3 describes an HPLC analytical method suitable for determining the caffeine content in green paraxanthine beans, paraxanthine coffees, and intermediates produced during the practice of the methods of the present disclosure. In addition to the disclosed HPLC analytical method, The International Organization for Standardization (ISO) method 20481 provides another suitable HPLC analytical method.

Moisture Content

A third aspect of the paraxanthine coffee is moisture content. As used herein, "moisture" refers to the mass of green coffee beans, green solvated paraxanthine coffee beans, green paraxanthine coffee beans, whole bean paraxanthine coffee, and/or ground paraxanthine coffee that is volatilized upon heating said whole bean or ground paraxanthine coffee at a temperature of 120° C. In some embodiments, moisture content refers to the mass of a whole bean paraxanthine coffee that is volatilized after heating a 3-10 g sample of said whole bean paraxanthine coffee at a temperature of 120° C. until the rate of mass loss decreases to less than 1 mg per 30 seconds. In some embodiments, moisture content refers to the mass of a ground paraxanthine coffee that is volatilized after heating a 3-10 g sample of ground paraxanthine coffee at a temperature of 120° C. until the rate of mass loss decreases to less than 1 mg per 30 seconds. One skilled in the art will recognize that, as used herein, the term moisture includes infusion solvents (non-limiting examples of which include water, ethyl acetate, methylene chloride, and carbon dioxide) used as described herein. The moisture content may be expressed as the amount in volatilized mass lost after heating at 120° C. as compared to the initial, starting mass prior to heating at 120° C.

Moisture contents greater than about 10% (w/w) may result in an undesired decrease in product shelf-life and/or product quality due to, for example, the accelerated release of volatile compounds that contribute to aroma and taste of paraxanthine coffee beverages. Additionally, moisture contents greater than 10% (w/w) may promote microbial growth on the infused paraxanthine, thereby diminishing the paraxanthine content. Generally speaking, it is desirable to have a moisture content less than 10% w/w, and typically less than 6% w/w, to prolong the product shelf life and/or reduce the rate of paraxanthine degradation.

In embodiments of the present disclosure, the moisture content in the disclosed paraxanthine coffee is less than about 10% (w/w). In some embodiments, the moisture content is less 9.0% (w/w). In some embodiments, the moisture content is less 8.0% (w/w). In some embodiments, the moisture content is less 7.0% (w/w). In some embodiments, the moisture content is less 6.0% (w/w). In some embodiments, the moisture content is less 5.0% (w/w). In some embodiments, the moisture content is less 4.5% (w/w). In some embodiments, the moisture content is less 4.0% (w/w). In some embodiments, the moisture content is less 3.5% (w/w). In some embodiments, the moisture content is less 3.0% (w/w).

Color

A fourth aspect of the paraxanthine coffee is the color. Consumers expect paraxanthine coffees to have a similar appearance to conventional, caffeinated coffees (i.e., those that been roasted without being infused with paraxanthine). While different methods are used in industry to assess coffee color, the Agtron scale (see, Santoso, et al., IOP Conf. Ser: Earth Environ. Sci., 924 (2021), 012058; DOI 10.1088/1755-1315/924/1/012058) is a simple and readily employed method. The Agtron scale is a 0-to-100-point scale wherein darker beans have a lower score and lighter beans have a higher score.

During the infusing, drying, and roasting steps described herein a number of process parameters boundary conditions are provided that contribute to the formation of paraxanthine coffee that is visually appealing. A paraxanthine coffee with an Agtron scale score greater than 90 may be unappealing to consumers. Likewise, a paraxanthine coffee with an Agtron scale score less than 20 may look burned be unappealing to consumers.

In many embodiments of the present disclosure, the disclosed paraxanthine coffees have an Agtron scale score between 20 and 90.

Methods of Producing Paraxanthine Coffees and Coffee Beverages

The disclosed paraxanthine coffees and paraxanthine coffee beverages are produced by adding paraxanthine to coffee beans. The paraxanthine may be added to coffee beans using a range of methods including, but not limited to, solid-solid grinding, paraxanthine absorption, or paraxanthine adsorption. Importantly, the method used should result in a paraxanthine coffee that is visually appealing to the consumer and wherein the paraxanthine is evenly distributed with the coffee beans. The coffee beans may be caffeinated, partially decaffeinated, or entirely decaffeinated to a final caffeine content of less than 0.1% w/w.

Solid-Solid Grinding Method

For solid-solid grinding, solid paraxanthine is directly ground into roasted coffee beans, and compression and friction are used to break apart and mix the coffee beans with paraxanthine. The grinding process also renders the paraxanthine, which is naturally white, "coffee colored," thereby increasing the suitability of its appearance to the consumer. Suitable solid-solid grinding techniques include, but are not limited to, mortar and pestle, ball mill, rod mill, and vertical roller mills.

When solid-solid grinding is used, the paraxanthine may be mixed with the coffee beans in one step or two steps. For the one step process, the paraxanthine-to-coffee ratio is between 0.5% w/w and 4.0% w/w. For the two step process, a first mixture is generated that has a high paraxanthine-to-coffee ratio, and this first mixture is then mixed with additional decaffeinated coffee to generate a second, final mixture comprising the desired 0.5% w/w to 4.0% w/w paraxanthine. Typically, when using two-step solid-solid grinding, the ratio of paraxanthine to coffee beans in the first mixture is between 10% and 30% by weight, which is sufficient to achieve the desired coffee color. The resulting first paraxanthine coffee mixture is then mixed with additional, ground coffee to achieve the desired paraxanthine w/w content. For example, a paraxanthine coffee with 20% w/w paraxanthine is first generated using a mortar and pestle to grind 3.75 g paraxanthine with 15 g decaffeinated coffee. The resulting 20% w/w paraxanthine coffee is then used to produce a 1.5% w/w paraxanthine coffee by mixing 1 gram of the 20% w/w paraxanthine coffee with 12.33 g of decaffeinated coffee, thereby producing 13.33 gram of paraxanthine coffee comprising 1.5% w/w paraxanthine.

Solid-solid grinding may be applied to any ground coffee, and it is easily implementable in paraxanthine coffee and paraxanthine coffee beverage large-scale production.

Paraxanthine Infusion Method

In one aspect, the disclosure provides a method of producing a whole bean paraxanthine coffee comprising the steps of:
1) Infusing a green coffee bean with paraxanthine and an infusion solvent to produce a green solvated paraxanthine coffee bean;
2) Drying the green solvated paraxanthine coffee bean to produce a green paraxanthine coffee bean; and,
3) Roasting the green paraxanthine coffee bean to produce a whole bean paraxanthine coffee.

In some instances, wherein a ground paraxanthine coffee is desired, the paraxanthine infusion method comprises the additional step of grinding the whole bean paraxanthine coffee to produce a ground paraxanthine coffee.

Paraxanthine Infusion Method Step 1: Infusing

In a first step, a green coffee bean is infused with paraxanthine and one or more infusion solvents. The output of this first step is a green solvated paraxanthine coffee bean. As used herein, the term "green solvated paraxanthine coffee bean" refers to a green coffee bean comprising at least 12.5% (w/w) moisture content, at least 0.025% (w/w) paraxanthine, and less than 2.5% (w/w) caffeine.

The paraxanthine infusing step takes place by generating an infusion mixture that comprises at least green coffee beans, one or more infusion solvents, and paraxanthine. In many instances, the infusion mixture additionally comprises a green coffee extract. The green coffee beans are incubated in the infusion mixture under conditions and for a time period sufficient to allow for infusion solvent and dissolved paraxanthine to diffuse into the green coffee bean.

Many infusion solvents are suitable for use in accordance with the methods of the disclosure. Since paraxanthine coffees and paraxanthine coffee beverages derived from said paraxanthine coffees are meant for human consumption, it is important the infusion solvent be suitable for use in food manufacturing. Non-limiting examples of suitable infusion solvents include water, ethyl acetate, methylene chloride, liquid carbon dioxide, acetone, benzyl alcohol, 1,3-butylene glycol, castor oil, citric acid esters, ethanol, glycerin, hexane, isopropanol, methanol, 2-butanone, and 1,2-propanediol. The infusion mixture may comprise any number of infusion solvents, including one infusion solvent, two infusion solvents, or more than two infusion solvents.

In various embodiments of the present disclosure, the infusion solvent is selected from a group consisting of water, ethyl acetate, ethanol, methylene chloride, liquid carbon dioxide, and mixtures thereof.

Three preferred infusion solvents are water, ethyl acetate, and ethanol due to their relatively low toxicity, ability to be produced from renewable resources, and their ability to dissolve paraxanthine at high concentrations. In some embodiments, the infusion solvent is water. In some embodiments, the infusion solvent is ethyl acetate. In some embodiments, the infusion solvent is ethanol. In some embodiments, the infusion solvent is a mixture of water and ethyl acetate. In some embodiments, the infusion solvent is a mixture of water and ethanol. In some embodiments, the infusion solvent is a mixture of ethyl acetate and ethanol. In still further embodiments, the infusion solvent is a mixture of water, ethyl acetate, and ethanol. In instances where the infusion solvent is a mixture of water, ethyl acetate, and ethanol the proportion of each individual member may range from 0% to 100% (i.e., it may comprise none, all, or part of the infusion solvent mixture).

In other embodiments, the infusion solvent is methylene chloride or liquid carbon dioxide.

In addition to the infusion solvent, the infusion mixture also comprises green coffee beans. The green coffee beans may be of any varietal suitable for human consumption, including, for example, coffee beans derived from *Coffea arabica, Coffea robusta* (also referred to as *Coffea canephora*), Coffee *liberica*, and *Coffea charrieriana* species. In many embodiments, the green coffee beans are derived from *Coffea arabica* species. In other embodiments, the green coffee beans are derived from Coffee *robusta* species.

To promote efficient infusion of the infusion solvent and dissolved paraxanthine into the bean, it is preferable for the moisture content of the green coffee beans to be below about 20% (w/w), more preferably below about 12.5% (w/w).

The amount, or mass fraction, of green coffee beans in the infusion mixture may be any amount that results in paraxanthine infusion into the coffee bean. To reduce the volume required for infusion, the mass fraction of green coffee beans relative to the total mass of the infusion mixture is typically greater than 0.1% (w/w).

In addition to the infusion solvent and green coffee beans, the infusion mixture additionally comprises paraxanthine. The paraxanthine can be of biological, synthetic, or semi-synthetic origin, or any mixture of biological, synthetic, or semi-synthetic paraxanthine. The paraxanthine can be anhydrous paraxanthine, a paraxanthine salt (including, for example, a sodium, potassium, calcium, or magnesium salt), a paraxanthine hydrate, or any mixture thereof.

A key parameter affecting the efficiency of paraxanthine infusion into the green coffee bean is the paraxanthine concentration in the infusion solvent within the reaction mixture. Green coffee beans are structurally limited in how much liquid may be absorbed into the bean; thus, if the paraxanthine concentration in the infusion solvent is too low, insufficient paraxanthine will enter the green coffee bean. In many embodiments of the present disclosure, the concentration of paraxanthine in the infusion solvent is greater than 0.1 mM. In some embodiments, the concentration paraxanthine in the infusion solvent is greater than 0.5 mM, greater than 1 mM, or greater than 5 mM.

In many instances, it is advantageous for the paraxanthine added to the infusion mixture to be of high purity and comprise low levels of small-molecule contaminants, including caffeine. In some embodiments, paraxanthine purity is greater than 95% (w/w), greater than 97.5% (w/w), greater than 98% (w/w), greater than 99% (w/w), or greater than 99.5% (w/w).

In addition to green coffee beans, an infusion solvent, and paraxanthine, the infusion mixture may additionally comprise green coffee extract. Green coffee extract is readily known to those skilled in the art and is a commercial supplement sold for human consumption, among other uses. Green coffee extract consists of a variety of infusion-solvent-soluble small molecules and proteins that contribute to the aroma and taste of paraxanthine coffee and derivative paraxanthine coffee beverages. Thus, green coffee extract may be included to the infusion mixture to improve the quality of the disclosed paraxanthine coffees.

The methods of the disclosure are not limited by the type of green coffee extract, its origin, composition, or mass fraction in the infusion mixture. Green coffee extract is often produced from conventional, caffeinated green coffee beans; thus, it is not uncommon for green coffee extract to comprise significant amounts of caffeine. Dependent on the desired caffeine content in the finished paraxanthine coffee, it may be desirable to use a green coffee extract with a low caffeine content to limit the amount of caffeine absorbed into the green coffee bean during the infusing step. In some embodiments, the green coffee extract comprises caffeine at a concentration less than 100 mM, less than 50 mM, less than 25 mM, less than 10 mM, less than 5 mM, less than 1 mM, or less than 0.1 mM.

As described herein, the infusing step entails incubating an infusion mixture comprising green coffee beans, one or more infusion solvents, paraxanthine, and optionally green coffee extract, under conditions and for a period of time that allow for paraxanthine and the infusion solvent to diffuse into the green coffee bean and generate a green solvated paraxanthine coffee bean. Two important process conditions that affect the efficiency and performance of this step are infusion mixture pH and temperature.

A first important parameter of the infusing step is the infusion mixture pH. At low pH values (for example, less than pH 4), the rate of acid-catalyzed reactions may increase to appreciable rates. Likewise, at high pH values (for example, greater than pH 10), the rate of base-catalyzed reactions may increase to appreciable rates. Both acid- and base-catalyzed reactions can decrease the quality of the final paraxanthine coffee and thus, generally speaking, are undesirable. For this reason, the infusing step is typically performed at pH values between pH 4 and pH 10.

Surprisingly, we discovered that the solubility of paraxanthine in the infusion solvents provided by the present disclosure increases with increasing pH. Thus, performing the infusing step at a pH of 7 or higher can be useful to increase the paraxanthine content of the finished paraxanthine coffee. In various embodiments, the pH of the infusion mixture is greater than pH 7. In some embodiments, the pH of the infusion mixture is greater than pH 8. In some embodiments, the pH of the infusion mixture is greater than 8.5. In some embodiments, the pH of the infusion mixture is greater than 9.0. In some embodiments, the pH of the infusion mixture is greater than 9.5.

A second important parameter of the infusing step is temperature. Generally speaking, the rate at which the infusion solvent comprising the dissolved paraxanthine enters the coffee bean increases with increasing temperature, leading to shorter process times. Additionally, the solubility of paraxanthine increases with increasing temperature, a characteristic useful for increasing the paraxanthine content of the finished paraxanthine coffee. However, if the green coffee beans are held at elevated temperatures for extended periods of time deterioration in the quality of the finished paraxanthine coffee may occur. Thus, it is typically preferred to perform the infusing step at temperatures between 4° C. and 95° C.

In various embodiments, the temperature of the infusion mixture is between about 4° C. and about 95° C. In some embodiments, the temperature of the infusion mixture is between 4° C. and 80° C. In some embodiments, the temperature of the infusion mixture is between 4° C. and 70° C. In some embodiments, the temperature of the infusion mixture is between 4° C. and 60° C. In some embodiments, the temperature of the infusion mixture is between 4° C. and 50° C. In some embodiments, the temperature of the infusion mixture is between 4° C. and 40° C. In some embodiments, the temperature of the infusion mixture is between 4° C. and 30° C. In some embodiments, the temperature of the infusion mixture is between 25° C. and 90° C. In some embodiments, the temperature of the infusion mixture is between 25° C. and 80° C. In some embodiments, the temperature of the infusion mixture is between 25° C. and 70° C. In some embodiments, the temperature of the infusion mixture is between 25° C. and 60° C. In some embodiments, the temperature of the infusion mixture is between 25° C. and 50° C. In some embodiments, the temperature of the infusion mixture is between 40° C. and 90° C. In some embodiments, the temperature of the infusion mixture is between 50° C. and 85° C. In some embodiments, the temperature of the infusion mixture is between 60° C. and 85° C.

The infusing step is complete when the desired paraxanthine content in the coffee bean is achieved. The time required to achieve the desired paraxanthine content is dependent on the pH, temperature, and paraxanthine concentration. Typically, the infusing step is completed in under 24 hours, and often in less than 12 hours. However, the methods of the disclosure are not to be limited by any specific time requirement for completion of the infusing step.

Paraxanthine Infusion Method Step 2: Drying

The input to the second, drying, step is a green solvated paraxanthine coffee bean with a moisture content greater than 12.5% (w/w), a paraxanthine content greater than 0.025% (w/w), and a caffeine content less than 2.5% (w/w). The output of the drying step is a green paraxanthine coffee bean. As used herein, the term "green paraxanthine coffee bean" refers to a green coffee bean comprising at least 0.05% (w/w) paraxanthine, less than 12.5% (w/w) moisture, and less than 2.5% (w/w) caffeine.

The drying step is performed by incubating a green solvated paraxanthine coffee bean at a temperature of less than 150° C. in order to remove some, a majority, or all of the infusion solvent from the green coffee bean. As described herein, the drying step is important to producing a paraxanthine coffee suitable for human consumption, to mitigate paraxanthine degradation in the green coffee bean, and, in some instances, to reduce the formation of flammable gases during roasting.

When the infusion solvent is water, it is important to decrease the water content to less than 12.5% w/w prior to roasting for at least three reasons (although the disclosure is not to be limited by any theory of mechanism of action). First, paraxanthine is rich in carbon, oxygen, and nitrogen, making paraxanthine particularly susceptible to catabolism by numerous naturally occurring bacterial and fungal species. When the infusion solvent is water, a water content greater than 12.5% w/w facilitates bacterial and/or fungal catabolism of the infused paraxanthine while simultaneously contaminating the green coffee bean. Decreasing the water content in the beans to less than 12.5% w/w enables the beans to be stored prior to roasting. Second, roasting beans with a greater than 12.5% w/w water content can result in scorching of the exterior surface while the inside remains unroasted. Third, roasting a paraxanthine-infused green coffee bean with greater than a 12.5% w/w water content can result in a roasted paraxanthine coffee containing a high moisture content (for example, greater than 10% w/w moisture), decreasing product quality and increasing the risk of product spoilage.

When the infusion solvent, or mixture of infusion solvents, comprises an organic solvent (non-limiting examples of which include ethyl acetate, methylene chloride, and ethanol), the organic solvent content in the green paraxanthine coffee bean should be reduced prior to roasting. High organic solvent contents in green paraxanthine coffee beans can pose a potential safety risk during roasting due to formation of flammable gases; additionally, governmental regulations strictly limit the organic solvent contents allowed in finished food products. Organic solvents may be stripped from green solvated paraxanthine coffee beans by steam stripping and then drying the beans to reduce the moisture content.

The drying step is performed by incubating the green solvated paraxanthine coffee bean at a temperature of less than 150° C. for any period of time necessary to achieve a less than 12.5% w/w moisture content. It is important that the drying step not be performed at temperatures greater than 150° C. as the combination of temperature and infusion solvent will result in a range of undesired thermochemical reactions within the bean that will diminish the paraxanthine coffee quality.

The drying step may be performed at any pressure so long as the moisture content after the completion of this step is less than 12.5% w/w. Performing the drying step at atmospheric pressure has the advantage of being easy to operate, it requires low-cost equipment, and it has a relatively low energy requirement. In many embodiments, the drying step is performed at atmospheric pressure. The drying step may also be performed at a pressure less than atmospheric pressure, which has the advantages of accelerating the drying rate and/or decreasing the rate of decomposition reactions within the coffee bean. In some embodiments, the drying step is performed at below atmospheric pressure. In some embodiments, the drying step is performed at vacuum levels between 50 and 300 mTorr. In some of these embodiments, the drying step is performed at vacuum levels between 100 mTorr and 200 mTorr.

Those skilled in the art will recognize that the green solvated paraxanthine coffee beans may be dried one time or more than once, and that the drying step may be performed continuously or in several, discrete phases. The methods of the present disclosure are not to be limited by the number of times the drying step is performed, the length of time the drying step(s) is performed, or whether drying is performed continuously or using several, discrete drying phases.

The output of the second, drying, step is a green paraxanthine coffee bean comprising a moisture content less than 12.5% w/w, a paraxanthine content greater than 0.05% w/w, and a caffeine content less than 2.5% w/w.

Paraxanthine Infusion Method Step 3: Roasting

The input to the third, roasting, step is a green paraxanthine coffee bean; the output of the third step is a whole bean paraxanthine coffee. The roasting step is performed by incubating a green paraxanthine coffee bean at a temperature of between 150° C. and 400° C. for a time period of at least two minutes.

The methods of the present disclosure are not to be limited by the time period between the drying step and the roasting step, nor are the methods to be limited by the equipment or vessel used to perform the drying and roasting steps. In some instances, the roasting step occurs immediately after the drying step. In this case, the same equipment used for the drying step is also used for the roasting step. In other instances, the roasting step is performed after the drying step using different equipment.

In the roasting step, a green paraxanthine coffee bean is incubated at a temperature of between 150° C. and 400° C. for a time period of at least 2 minutes. Those skilled in the art will recognize that the distinction between the roasting step and the preceding drying step is the process temperature and time; the drying step is performed at temperatures less than 150° C. for any length of time and the roasting step is performed at temperatures between 150° C. and 400° C. for a period of at least two minutes.

The temperature of the roasting step is important because the physicochemical reactions that are needed to produce a paraxanthine coffee with consumer appeal occur between 150° C. and 400° C. Although the methods of the disclosure are not to be limited by any mechanism of action, examples of physicochemical reactions that take place during roasting include maillard reactions between sugars and proteins (producing, for example, 2-furfurytlthiol, a small-molecule contributing to coffee aroma), sugar caramelization, bean splitting, pyrolysis, cellulose deconstruction, and color development. These reactions either do not occur, or do not occur at an appreciable rate, at temperatures below 150° C. At temperatures greater than 400° C., undesired paraxanthine decomposition may occur at appreciable rates.

The output of the roasting step is a whole bean paraxanthine coffee suitable for direct consumption, grinding to produce a ground paraxanthine coffee, and/or brewing to produce a paraxanthine coffee beverage.

Optional Paraxanthine Infusion Method Step 4: Grinding

In some instances, a whole bean paraxanthine coffee is desirable in that it can be readily stored, packed, and delivered to consumers. In other stances, it is desirable to grind the whole paraxanthine coffee, producing a form factor more readily amenable to brewing using any number of methods known to those skilled in the art. Thus, in some embodiments, the paraxanthine infusion methods consists of an additional, fourth, step in which grinding is used to convert a whole bean paraxanthine coffee to a ground paraxanthine coffee.

The methods of the present disclosure are not restricted by any particular method to grinding whole bean paraxanthine coffee, and those skilled in the art will recognize grinding methods and grinders used with conventional coffee beans are equally applicable toward use with whole bean paraxanthine coffee. Examples of suitable grinders include, but are not limited to, burr grinders, conical burr grinders, flat burr grinders, and blade grinders.

The output of this optional, fourth step is a ground paraxanthine coffee having an average particle size of less than 1.5 mm. ISO method 23134 describes suitable methods for measuring particle sizes.

Paraxanthine Absorption Method

For addition of paraxanthine to coffee beans by absorption, green, unroasted coffee beans are soaked in a concentrated paraxanthine aqueous solution to allow paraxanthine diffusion into the coffee beans until a concentration equilibrium is reached. The absorption method is typically performed using raw, or green, decaffeinated, partially decaffeinated, or caffeinated coffee beans.

Green coffee beans may be immersed in an aqueous solution comprising at least 1 g/l paraxanthine, and as high as 100 g/l or more paraxanthine. Paraxanthine concentration may be increased to accelerate the rate of paraxanthine diffusion into the coffee beans and prevent desirable natural coffee flavorants from leaking out.

The temperature of the aqueous phase is typically greater than 25° C., often greater than 50° C., and may be as high as 900 or 100° C. or higher, if pressure is applied to reduce or eliminate water vaporization, to increase paraxanthine solubility and accelerate the rate of diffusion.

A green coffee extract that comprises some or all the water-soluble components of green coffee beans may additionally be included in the paraxanthine solution to prevent the leakage or reduce the loss of coffee flavorants from the coffee beans while in solution.

Paraxanthine absorption may be performed simultaneously with coffee bean decaffeination, thereby reducing the number of manufacturing steps and the length of the preparation process.

Paraxanthine Adsorption Method

For addition of paraxanthine to coffee beans by adsorption, unroasted or roasted coffee beans are coated with a concentrated solution of paraxanthine on the outer surface of the beans, and the carrier solvent is then allowed to evaporate, leaving a thin layer of paraxanthine on the coffee bean external surface. During the adsorption process described herein a portion of the paraxanthine and/or carrier solvent may also be absorbed into the interior of the bean. Thus, one skilled in the art will recognize that absorption and adsorption may occur contemporaneously.

Suitable carrier solvents for paraxanthine adsorption include, but are not limited to, water, supercritical carbon dioxide, subcritical carbon dioxide, ethyl acetate, ethanol, glycerol, propylene glycol, and methylene chloride.

In some embodiments, the carrier solvent is water, and the paraxanthine concentration in the carrier solvent is typically greater than 10 g/l and as high as 100 g/l or greater. The amount of carrier solvent applied to the decaffeinated coffee beans is determined by the paraxanthine concentration in the carrier solvent and the desired paraxanthine content in the final paraxanthine coffee product. For example, if the desired paraxanthine content of the paraxanthine coffee is 1.5% w/w and the paraxanthine concentration in the carrier solvent is 25 g/l, 60 ml of the carrier solvent are applied to the coffee beans to produce 100 grams of paraxanthine coffee.

The carrier solvent comprising paraxanthine may be applied using any number of suitable approaches including, but not limited to, spray coating and rotating drum mixer.

The disclosed methods may further comprise partially or entirely decaffeinating green coffee beans prior to or during paraxanthine addition.

Coffee beans may be decaffeinated by extracting out caffeine from the green coffee beans into a solvent. Suitable solvents include, but are not limited to, water, ethyl acetate, methylene chloride, benzyl alcohol, supercritical carbon dioxide and subcritical carbon dioxide.

Organic solvents, however, are expensive, environmentally toxic, and their use in large quantities at industrial scale pose inherent risks to human health and safety. Furthermore, many consumers have a negative perception of organic solvents. In addition, residual amounts of organic solvent must be removed to meet governmental regulations and requirements.

Water is an excellent solvent alternative for decaffeination of coffee beans, as it is non-toxic, low cost, and environmentally benign. Moreover, the quality of the final product is not adversely affected by residual quantities of water remaining after caffeine extraction.

Thus, in some embodiments, green coffee beans are partially or entirely decaffeinated using water as the solvent. In some embodiments, paraxanthine is adsorbed into green coffee beans during the decaffeination process.

Examples of commercial, water-based processes for coffee bean decaffeination that may be used to produce the disclosed paraxanthine coffees include the Swiss Water Process and the Mountain Water Process. These commercial processes allow adsorption of paraxanthine into the coffee beans contemporaneous to the removal of caffeine.

When water is used as solvent for the decaffeination process, the green coffee beans are typically "hydrated" prior to decaffeination. Coffee beans have a natural moisture content of 8%-12% by weight. Hydrated green coffee beans are generated by swelling the green coffee beans by exposure to water or steam to achieve a moisture content of about 20% to about 40%. While not wishing to be bound by any theory, the swelling of the coffee beans with water is thought to open the bean structure to allow more efficient diffusion of the caffeine from the bean into the water used for decaffeination.

Decaffeination is carried out by contacting hydrated or non-hydrated green coffee beans with water for a sufficient time to completely or partially remove caffeine to the desired level. Those skilled in the art will recognize that contact time will depend, in part, on the caffeine content of the original coffee beans, the ratio of water-to-beans in the system, and the process temperature and pressure, among other factors recognized in the decaffeination arts. An appropriate contact time can be readily determined by measuring the caffeine content of the coffee beans during the time course of the decaffeination.

Typically, decaffeination is carried out at pressures of about 1-5 atmospheres and temperatures ranging from about 20° C. to about 125° C. Caffeine is substantially more soluble in water at elevated temperatures and thereby extraction times are decreased, thus higher operating temperatures (i.e. above 50° C.) are generally preferred.

Decaffeination can be performed in a continuous, semi-continuous, or batch manner. The water-to-bean ratio is kept to a minimum of 3:1, and typically, a ratio within the range of from 3:1 to 8:1, and often, a ratio of from 3:1 to 5:1.

Following contact with water, the resulting wet green coffee beans have a moisture content from about 40% to about 55%. The beans are then dried to decrease the water content to between about 8% and about 15% by weight.

The water used for decaffeination will typically comprise additives, including, but not limited to, decaffeinated green coffee extract and/or paraxanthine.

Decaffeinated green coffee extract comprises all, or a fraction of, the water soluble compounds that will diffuse out of the green coffee bean and into the water during decaffeination. Decaffeinated green coffee extracts may be added to the water to selectively remove caffeine from the coffee beans and leave desirable flavorants in the coffee beans, thereby producing more flavorful paraxanthine coffees and paraxanthine coffee beverages. The caffeine content of the decaffeinated green coffee extract is kept to a minimum to promote the efficient removal of caffeine from the green coffee bean.

In some embodiments, the water used for decaffeination comprises paraxanthine. The inclusion of paraxanthine in the water enables the diffusion of paraxanthine into the green coffee beans contemporaneous with the diffusion of caffeine out of the green coffee beans. By adjusting the paraxanthine concentration in decaffeination water, the contact time, and the number of rounds of treatment, among other parameters, the desired paraxanthine content in the resulting, paraxanthine coffee beans may be achieved. For example, to achieve a paraxanthine content of between 0.5% w/w to 4.0% w/w in a single decaffeination step, the paraxanthine concentration in the decaffeination water should be at least 1 g/l, and as high as 100 g/l or more paraxanthine.

The disclosed methods may further comprise adding additional additives, excipients and/or flavorants to the disclosed paraxanthine coffees and paraxanthine coffee beverages, to improve the taste, health benefits, and/or performance of the disclosed paraxanthine coffees and paraxanthine coffee beverages. Suitable additives include, but are not limited to, L-theanine, turmeric, vitamin B1, vitamin B3, vitamin B5, vitamin B12, biotin, resveratrol, as well as other vitamins, such as vitamin A, vitamin C, vitamin D, vitamin E, and the like. Various salts may also be added to the disclosed paraxanthine coffees to decreases any bitter taste. Examples of suitable salts include, but are not limited to, sodium chloride, potassium chloride, magnesium chloride, and calcium chloride.

Also provided herein are paraxanthine coffees and paraxanthine coffee beverages produced by the disclosed methods.

Paraxanthine Sport Drinks and Paraxanthine Energy Drinks

The disclosed paraxanthine beverages include, but are not limited to, paraxanthine sport drink and paraxanthine energy drink formulations. Such paraxanthine sport and energy drinks provide consumers with nutrition and mental and physical stimulation, including increased attention, increased reaction speed, and increased muscle strength and endurance, and help improve the physical and mental well-being of the consumers.

The disclosed paraxanthine sport drinks and paraxanthine energy drinks comprise at least 70% (w/w), at least 75% (w/w), or at least 80% (w/w) water, from about 0.1 mg/ml to about 5 mg/ml, or from about 25 mg/serving to about 600 mg/serving paraxanthine, from about 0.01 g/ml to about 0.2 g/ml sweeteners and, optionally, additives, flavorants, excipients, and the like.

Suitable sweeteners include, but are not limited to, natural and synthetic sweeteners, such as, for example, glucose, sucrose, fructose, maltose, maltodextrin, lactose, L-alanine, D-alanine, glycine, L-serine, D-serine, glycyrrhizin, steviol glycosides, thaumatin, sodium cyclamate, aspartame, acesulfame-K, neotame, advantame, saccharin, sucralose, sorbitol, mannitol, xylitol, erythritol, lactitol, maltitol, mogrosides, lugduname, carrelame, bernardame, sucronate, neohesperidin dihydrochalcone, and any combinations thereof.

Suitable additives include, but are not limited to, alkylxanthines, vitamins, dietary ingredients, herbal extracts, acidulants, antioxidants, and preservatives.

Suitable alkylxanthines include, but are not limited to, caffeine, theobromine, and theophylline. In some embodiments, the total alkylxanthine content in the disclosed paraxanthine energy drinks and paraxanthine sport drinks is from about 0.04 mg/ml to about 1.1 mg/ml, or from about 10 mg/serving to about 250 mg/serving.

In some embodiments, the disclosed paraxanthine sport drinks and paraxanthine energy drinks comprise caffeine in an amount from about 0.04 mg/ml to about 1.1 mg/ml, or from about 10 mg/serving to about 250 mg/serving.

In some embodiments, the disclosed paraxanthine sport drinks and paraxanthine energy drinks comprise caffeine in a caffeine content to paraxanthine content ratio from about 0.01:1 to about 100:1 (mol/mol).

The disclosed paraxanthine sport drinks and paraxanthine energy drinks may optionally comprise one or more vitamins selected from the group consisting of vitamin B12 (including methylcobalamin and cyanocobalamin), vitamin B6 (including pyridoxine, pyridoxamine, and pyridoxal), vitamin B3 (including niacin, niacinamide, and nicotinamide riboside), vitamin B8 (inositol), vitamin B2 (riboflavin), and vitamin B5 (pantothenic acid), in an amount from about 1 g/serving to about 50 mg/serving.

The disclosed paraxanthine sport drinks and paraxanthine energy drinks may additionally comprise one or more dietary ingredients, such as taurine in an amount from about 0.5 g/serving to about 5 g/serving, glucuronolactone, and L-carnitine in an amount from about 10 mg/serving to about 100 mg/serving.

In some embodiments, the disclosed paraxanthine sport drinks and paraxanthine energy drinks may additionally comprise one or more additives selected from the group consisting of herbal extracts, acidulants, antioxidants, and preservatives.

Suitable herbal extracts include, but are not limited to, ginseng extract, guarana extract, milk thistle extract, green tea extract, green coffee extract, coffee extract, and ginger extract, among others.

Suitable acidulants include, but are not limited to, acetic acid, lactic acid, malic acid, fumaric acid, citric acid, tartaric acid, phosphoric acid, and succinic acid, in an amount ranging from about 0.25% (w/w) to about 1% (w/w).

Suitable antioxidants include, but are not limited to, ascorbic acid, sodium ascorbate, calcium ascorbate, fatty acid esters of ascorbic acid, tocopherols, alpha-tocopherol, gamma-tocopherol, delta-tocopherol, propyl gallate, erythorbic acid, sodium erythorbate, tertiary-butyl hydroquinone (TBHQ), butylated hydroxyanisole (BHA), butylated hydroxytoluene (BHT), extracts of rosemary, and 4-hexylresorcinol.

Suitable preservatives include, but are not limited to, sorbic acid, potassium sorbate, benzoic acid, sodium benzoate, potassium benzoate, calcium benzoate, sulphur dioxide, sodium sulphite, sodium hydrogen sulphite, propionic acid, sodium propionate, calcium propionate, potassium propionate, and lysozyme.

Use of the Disclosed Paraxanthine Coffees and Paraxanthine Coffee Beverages

Additionally provided herein are methods for increasing alertness, wakefulness, and productivity in a subject, without increasing anxiety, jitteriness, and irritability. The disclosed methods comprise administering to the subject the disclosed paraxanthine coffees and paraxanthine coffee beverages provided herein.

Suitable paraxanthine coffees and paraxanthine coffee beverages include, but are not limited to, brewed paraxanthine coffees, including hot and cold brewed paraxanthine coffees, espresso paraxanthine coffees, paraxanthine coffee drinks, instant paraxanthine coffees, ready-to-drink paraxanthine coffee beverages, roasted paraxanthine coffee beverages, paraxanthine milk shakes, paraxanthine energy drinks, paraxanthine diet drinks, paraxanthine supplement drinks, and paraxanthine sport beverages.

Administration may be self-administration or administration by others.

The paraxanthine coffees and paraxanthine coffee beverages provided herein present many advantages that make them suitable for consumption. The disclosed paraxanthine coffees and paraxanthine coffee beverages essentially contain no caffeine or have a low content of caffeine, and are enriched in coffee flavorants that make them appealable to the most demanding consumers. Because paraxanthine has a shorter half-life than caffeine, the disclosed paraxanthine coffees and paraxanthine coffee beverages do not leave consumers with undesirable side effects associated with caffeine consumption, such as increased anxiety, jitteriness, irritability, nervousness, and tremors, and are not toxic. Accordingly, the disclosed paraxanthine coffees and paraxanthine coffee beverages may be consumed several times a day to increase alertness.

NON-LIMITING LIST OF EXEMPLARY EMBODIMENTS

In addition to the aspects and embodiments described and provided elsewhere in this disclosure, the following non-limiting list of particular embodiments are specifically contemplated.

1. A paraxanthine coffee comprising:
1) from 0.005% (w/w) to 10% (w/w) paraxanthine; and,
2) less than 2.5% (w/w) caffeine.

2. A paraxanthine coffee comprising:
1) from 0.005% (w/w) to 10% (w/w) paraxanthine; and,
2) less than 1% (w/w) caffeine.

3. A paraxanthine coffee comprising:
1) from 0.005% (w/w) to 10% (w/w) paraxanthine; and,
2) less than 0.75% (w/w) caffeine.

4. A paraxanthine coffee comprising:
1) from 0.005% (w/w) to 10% (w/w) paraxanthine; and,
2) less than 0.5% (w/w) caffeine.

5. A paraxanthine coffee comprising:
1) from 0.005% (w/w) to 10% (w/w) paraxanthine; and,
2) less than 0.25% (w/w) caffeine.

6. A paraxanthine coffee comprising:
1) from 0.005% (w/w) to 10% (w/w) paraxanthine; and,
2) less than 0.1% (w/w) caffeine.

7. A paraxanthine coffee comprising:
1) from 0.005% (w/w) to 10% (w/w) paraxanthine; and,
2) less than 0.05% (w/w) caffeine.

8. A paraxanthine coffee comprising:
1) from 0.005% (w/w) to 10% (w/w) paraxanthine; and,
2) less than 0.01% (w/w) caffeine.

9. A paraxanthine coffee comprising:
1) from 0.005% (w/w) to 10% (w/w) paraxanthine; and,
2) less than 0.005% (w/w) caffeine.

10. A paraxanthine coffee comprising:
3) from 0.005% (w/w) to 10% (w/w) paraxanthine; and,
4) less than 0.001% (w/w) caffeine.

11. A paraxanthine coffee comprising:
1) from 0.1% (w/w) to 2% (w/w) paraxanthine; and,
2) less than 2.5% (w/w) caffeine.

12. A paraxanthine coffee comprising:
1) from 0.1% (w/w) to 2% (w/w) paraxanthine; and,
2) less than 1% (w/w) caffeine.

13. A paraxanthine coffee comprising:
1) from 0.1% (w/w) to 2% (w/w) paraxanthine; and,
2) less than 0.75% (w/w) caffeine.

14. A paraxanthine coffee comprising:
1) from 0.1% (w/w) to 2% (w/w) paraxanthine; and,
2) less than 0.5% (w/w) caffeine.

15. A paraxanthine coffee comprising:
1) from 0.1% (w/w) to 2% (w/w) paraxanthine; and,
2) less than 0.25% (w/w) caffeine.

16. A paraxanthine coffee comprising:
1) from 0.1% (w/w) to 2% (w/w) paraxanthine; and,
2) less than 0.1% (w/w) caffeine.

17. A paraxanthine coffee comprising:
1) from 0.1% (w/w) to 2% (w/w) paraxanthine; and,
2) less than 0.05% (w/w) caffeine.

18. A paraxanthine coffee comprising:
1) from 0.1% (w/w) to 2% (w/w) paraxanthine; and,
2) less than 0.01% (w/w) caffeine.

19. A paraxanthine coffee comprising:
1) from 0.1% (w/w) to 2% (w/w) paraxanthine; and,
2) less than 0.005% (w/w) caffeine.

20. A paraxanthine coffee beverage comprising:
1) from 0.005% (w/w) to 10% (w/w) paraxanthine; and,
2) less than 2.5% (w/w) caffeine.

21. A paraxanthine coffee beverage comprising:
1) from 0.005% (w/w) to 10% (w/w) paraxanthine; and,
2) less than 1% (w/w) caffeine.
22. A paraxanthine coffee beverage comprising:
1) from 0.005% (w/w) to 10% (w/w) paraxanthine; and,
2) less than 0.1% (w/w) caffeine.
23. A paraxanthine coffee beverage comprising:
1) from 0.005% (w/w) to 10% (w/w) paraxanthine; and,
2) less than 0.05% (w/w) caffeine.
24. A paraxanthine coffee beverage comprising:
1) from 0.005% (w/w) to 10% (w/w) paraxanthine; and,
2) less than 0.005% (w/w) caffeine.
25. A paraxanthine coffee beverage comprising:
1) from 0.005% (w/w) to 10% (w/w) paraxanthine; and,
2) less than 0.001% (w/w) caffeine.
26. A paraxanthine coffee beverage comprising:
1) from 0.005% (w/w) to 0.5% (w/w) paraxanthine; and,
2) less than 2.5% (w/w) caffeine.
27. A paraxanthine coffee beverage comprising:
1) from 0.005% (w/w) to 0.5% (w/w) paraxanthine; and,
2) less than 1% (w/w) caffeine.
28. A paraxanthine coffee beverage comprising:
1) from 0.005% (w/w) to 0.5% (w/w) paraxanthine; and,
2) less than 0.1% (w/w) caffeine.
29. A paraxanthine coffee beverage comprising:
1) from 0.005% (w/w) to 0.5% (w/w) paraxanthine; and,
2) less than 0.05% (w/w) caffeine.
30. A paraxanthine coffee beverage comprising:
1) from 0.005% (w/w) to 0.5% (w/w) paraxanthine; and,
2) less than 0.005% (w/w) caffeine.
31. A paraxanthine coffee beverage comprising:
1) from 0.005% (w/w) to 0.5% (w/w) paraxanthine; and,
2) less than 0.001% (w/w) caffeine.
32. A paraxanthine beverage comprising:
1) from 0.005% (w/w) to 10% (w/w) paraxanthine; and,
2) less than 2.5% (w/w) caffeine.
33. A paraxanthine beverage comprising:
1) from 0.005% (w/w) to 10% (w/w) paraxanthine; and,
2) less than 1% (w/w) caffeine.
34. A paraxanthine beverage comprising:
1) from 0.005% (w/w) to 10% (w/w) paraxanthine; and,
2) less than 0.1% (w/w) caffeine.
35. A paraxanthine beverage comprising:
1) from 0.005% (w/w) to 10% (w/w) paraxanthine; and,
2) less than 0.05% (w/w) caffeine.
36. A paraxanthine beverage comprising:
1) from 0.005% (w/w) to 10% (w/w) paraxanthine; and,
2) less than 0.005% (w/w) caffeine.
37. A paraxanthine beverage comprising:
1) from 0.005% (w/w) to 10% (w/w) paraxanthine; and,
2) less than 0.001% (w/w) caffeine.
38. A paraxanthine beverage comprising:
1) from 0.005% (w/w) to 0.5% (w/w) paraxanthine; and,
2) less than 2.5% (w/w) caffeine.
39. A paraxanthine beverage comprising:
1) from 0.005% (w/w) to 0.5% (w/w) paraxanthine; and,
2) less than 1% (w/w) caffeine.
40. A paraxanthine beverage comprising:
1) from 0.005% (w/w) to 0.5% (w/w) paraxanthine; and,
2) less than 0.1% (w/w) caffeine.
41. A paraxanthine beverage comprising:
1) from 0.005% (w/w) to 0.5% (w/w) paraxanthine; and,
2) less than 0.05% (w/w) caffeine.
42. A paraxanthine beverage comprising:
1) from 0.005% (w/w) to 0.5% (w/w) paraxanthine; and,
2) less than 0.005% (w/w) caffeine.
43. A paraxanthine beverage comprising:
1) from 0.005% (w/w) to 0.5% (w/w) paraxanthine; and,
2) less than 0.001% (w/w) caffeine.
44. A paraxanthine coffee bean comprising:
1) from 0.1% (w/w) to 3% (w/w) paraxanthine; and,
2) less than 2.5% (w/w) caffeine.
45. A paraxanthine coffee bean comprising:
1) from 0.1% (w/w) to 3% (w/w) paraxanthine; and,
2) less than 1.5% (w/w) caffeine.
46. A paraxanthine coffee bean comprising:
1) from 0.1% (w/w) to 3% (w/w) paraxanthine; and,
2) less than 1% (w/w) caffeine.
47. A paraxanthine coffee bean comprising:
1) from 0.1% (w/w) to 3% (w/w) paraxanthine; and,
2) less than 0.5% (w/w) caffeine.
48. A paraxanthine coffee bean comprising:
1) from 0.1% (w/w) to 3% (w/w) paraxanthine; and,
2) less than 0.25% (w/w) caffeine.
49. A paraxanthine coffee bean comprising:
1) from 0.1% (w/w) to 3% (w/w) paraxanthine; and,
2) less than 0.1% (w/w) caffeine.
50. A paraxanthine coffee bean comprising:
1) from 0.1% (w/w) to 3% (w/w) paraxanthine; and,
2) less than 0.05% (w/w) caffeine.
51. A paraxanthine coffee bean comprising:
1) from 0.1% (w/w) to 3% (w/w) paraxanthine; and,
2) less than 0.01% (w/w) caffeine.
52. A paraxanthine coffee bean comprising:
1) from 0.1% (w/w) to 3% (w/w) paraxanthine; and,
2) less than 0.005% (w/w) caffeine.
53. A paraxanthine coffee bean comprising:
1) from 0.5% (w/w) to 2.5% (w/w) paraxanthine; and,
2) less than 2.5% (w/w) caffeine.
54. A paraxanthine coffee bean comprising:
1) from 0.5% (w/w) to 2.5% (w/w) paraxanthine; and,
2) less than 2.5% (w/w) caffeine.
55. A paraxanthine coffee bean comprising:
1) from 0.5% (w/w) to 2.5% (w/w) paraxanthine; and,
2) less than 1.5% (w/w) caffeine.
56. A paraxanthine coffee bean comprising:
1) from 0.5% (w/w) to 2.5% (w/w) paraxanthine; and,
2) less than 1% (w/w) caffeine.
57. A paraxanthine coffee bean comprising:
1) from 0.5% (w/w) to 2.5% (w/w) paraxanthine; and,
2) less than 0.5% (w/w) caffeine.
58. A paraxanthine coffee bean comprising:
1) from 0.5% (w/w) to 2.5% (w/w) paraxanthine; and,
2) less than 0.25% (w/w) caffeine.
59. A paraxanthine coffee bean comprising:
1) from 0.5% (w/w) to 2.5% (w/w) paraxanthine; and,
2) less than 0.1% (w/w) caffeine.
60. A paraxanthine coffee bean comprising:
1) from 0.5% (w/w) to 2.5% (w/w) paraxanthine; and,
2) less than 0.05% (w/w) caffeine.
61. A paraxanthine coffee bean comprising:
1) from 0.5% (w/w) to 2.5% (w/w) paraxanthine; and,
2) less than 0.01% (w/w) caffeine.
62. A paraxanthine coffee bean comprising:
1) from 0.5% (w/w) to 2.5% (w/w) paraxanthine; and,
2) less than 0.005% (w/w) caffeine.
63. A ground paraxanthine coffee bean comprising:
1) from 0.1% (w/w) to 3% (w/w) paraxanthine; and,
2) less than 2.5% (w/w) caffeine.
64. A ground paraxanthine coffee bean comprising:
1) from 0.1% (w/w) to 3% (w/w) paraxanthine; and,
2) less than 1.5% (w/w) caffeine.

65. A ground paraxanthine coffee bean comprising:
1) from 0.1% (w/w) to 3% (w/w) paraxanthine; and,
2) less than 1% (w/w) caffeine.
66. A ground paraxanthine coffee bean comprising:
1) from 0.1% (w/w) to 3% (w/w) paraxanthine; and,
2) less than 0.5% (w/w) caffeine.
67. A ground paraxanthine coffee bean comprising:
1) from 0.1% (w/w) to 3% (w/w) paraxanthine; and,
2) less than 0.25% (w/w) caffeine.
68. A ground paraxanthine coffee bean comprising:
1) from 0.1% (w/w) to 3% (w/w) paraxanthine; and,
2) less than 0.1% (w/w) caffeine.
69. A ground paraxanthine coffee bean comprising:
1) from 0.1% (w/w) to 3% (w/w) paraxanthine; and,
2) less than 0.05% (w/w) caffeine.
70. A ground paraxanthine coffee bean comprising:
1) from 0.1% (w/w) to 3% (w/w) paraxanthine; and,
2) less than 0.01% (w/w) caffeine.
71. A ground paraxanthine coffee bean comprising:
1) from 0.1% (w/w) to 3% (w/w) paraxanthine; and,
2) less than 0.005% (w/w) caffeine.
72. A ground paraxanthine coffee bean comprising:
1) from 0.5% (w/w) to 2.5% (w/w) paraxanthine; and,
2) less than 2.5% (w/w) caffeine.
73. A ground paraxanthine coffee bean comprising:
1) from 0.5% (w/w) to 2.5% (w/w) paraxanthine; and,
2) less than 2.5% (w/w) caffeine.
74. A ground paraxanthine coffee bean comprising:
1) from 0.5% (w/w) to 2.5% (w/w) paraxanthine; and,
2) less than 1.5% (w/w) caffeine.
75. A ground paraxanthine coffee bean comprising:
1) from 0.5% (w/w) to 2.5% (w/w) paraxanthine; and,
2) less than 1% (w/w) caffeine.
76. A ground paraxanthine coffee bean comprising:
1) from 0.5% (w/w) to 2.5% (w/w) paraxanthine; and,
2) less than 0.5% (w/w) caffeine.
77. A ground paraxanthine coffee bean comprising:
1) from 0.5% (w/w) to 2.5% (w/w) paraxanthine; and,
2) less than 0.25% (w/w) caffeine.
78. A ground paraxanthine coffee bean comprising:
1) from 0.5% (w/w) to 2.5% (w/w) paraxanthine; and,
2) less than 0.1% (w/w) caffeine.
79. A ground paraxanthine coffee bean comprising:
1) from 0.5% (w/w) to 2.5% (w/w) paraxanthine; and,
2) less than 0.05% (w/w) caffeine.
80. A ground paraxanthine coffee bean comprising:
1) from 0.5% (w/w) to 2.5% (w/w) paraxanthine; and,
2) less than 0.01% (w/w) caffeine.
81. A ground paraxanthine coffee bean comprising:
1) from 0.5% (w/w) to 2.5% (w/w) paraxanthine; and,
2) less than 0.005% (w/w) caffeine.
82. A partially decaffeinated paraxanthine beverage comprising:
1) from 0.005% (w/w) to 10% (w/w) paraxanthine; and,
2) between 0.005% (w/w) and 0.15% (w/w) caffeine.
83. A partially decaffeinated paraxanthine beverage comprising:
1) from 0.005% (w/w) to 5% (w/w) paraxanthine; and,
2) between 0.005% (w/w) and 0.15% (w/w) caffeine.
84. A partially decaffeinated paraxanthine beverage comprising:
1) from 0.005% (w/w) to 1% (w/w) paraxanthine; and,
2) between 0.005% (w/w) and 0.15% (w/w) caffeine.
85. A partially decaffeinated paraxanthine beverage comprising:
1) from 0.005% (w/w) to 0.5% (w/w) paraxanthine; and,
2) between 0.005% (w/w) and 0.15% (w/w) caffeine.
86. The composition of any one of the preceding embodiments, wherein said paraxanthine is between 0.005% and 10% (w/w) of said composition.
87. The composition of any one of the preceding embodiments, wherein said paraxanthine is between 0.005% and 9% (w/w) of said composition.
88. The composition of any one of the preceding embodiments, wherein said paraxanthine is between 0.005% and 8% (w/w) of said composition.
89. The composition of any one of the preceding embodiments, wherein said paraxanthine is between 0.005% and 7% (w/w) of said composition.
90. The composition of any one of the preceding embodiments, wherein said paraxanthine is between 0.005% and 6% (w/w) of said composition.
91. The composition of any one of the preceding embodiments, wherein said paraxanthine is between 0.005% and 5% (w/w) of said composition.
92. The composition of any one of the preceding embodiments, wherein said paraxanthine is between 0.005% and 4% (w/w) of said composition.
93. The composition of any one of the preceding embodiments, wherein said paraxanthine is between 0.005% and 3% (w/w) of said composition.
94. The composition of any one of the preceding embodiments, wherein said paraxanthine is between 0.005% and 2% (w/w) of said composition.
95. The composition of any one of the preceding embodiments, wherein said paraxanthine is between 0.005% and 1.5% (w/w) of said composition.
96. The composition of any one of the preceding embodiments, wherein said paraxanthine is between 0.005% and 1% (w/w) of said composition.
97. The composition of any one of the preceding embodiments, wherein said paraxanthine is between 0.005% and 0.1% (w/w) of said composition.
98. The composition of any one of the preceding embodiments, wherein said paraxanthine is between 0.005% and 0.075% (w/w) of said composition.
99. The composition of any one of the preceding embodiments, wherein said paraxanthine is between 0.005% and 0.05% (w/w) of said composition.
100. The composition of any one of the preceding embodiments, wherein said paraxanthine is between 0.005% and 0.025% (w/w) of said composition.
101. The composition of any one of the preceding embodiments, wherein said paraxanthine is between 0.005% and 0.01% (w/w) of said composition.
102. The composition of any one of the preceding embodiments, wherein said paraxanthine is between 0.005% and 0.075% (w/w) of said composition.
103. The composition of any one of the preceding embodiments, wherein said paraxanthine is between 0.05% and 9% (w/w) of said composition.
104. The composition of any one of the preceding embodiments, wherein said paraxanthine is between 0.05% and 8% (w/w) of said composition.
105. The composition of any one of the preceding embodiments, wherein said paraxanthine is between 0.05% and 7% (w/w) of said composition.
106. The composition of any one of the preceding embodiments, wherein said paraxanthine is between 0.05% and 6% (w/w) of said composition.
107. The composition of any one of the preceding embodiments, wherein said paraxanthine is between 0.05% and 5% (w/w) of said composition.

108. The composition of any one of the preceding embodiments, wherein said paraxanthine is between 0.05% and 4% (w/w) of said composition.

109. The composition of any one of the preceding embodiments, wherein said paraxanthine is between 0.05% and 3% (w/w) of said composition.

110. The composition of any one of the preceding embodiments, wherein said paraxanthine is between 0.05% and 2% (w/w) of said composition.

111. The composition of any one of the preceding embodiments, wherein said paraxanthine is between 0.05% and 1.75% (w/w) of said composition.

112. The composition of any one of the preceding embodiments, wherein said paraxanthine is between 0.05% and 1.5% (w/w) of said composition.

113. The composition of any one of the preceding embodiments, wherein said paraxanthine is between 0.05% and 1.4% (w/w) of said composition.

114. The composition of any one of the preceding embodiments, wherein said paraxanthine is between 0.05% and 1.3% (w/w) of said composition.

115. The composition of any one of the preceding embodiments, wherein said paraxanthine is between 0.05% and 1.25% (w/w) of said composition.

116. The composition of any one of the preceding embodiments, wherein said paraxanthine is between 0.05% and 1.20% (w/w) of said composition.

117. The composition of any one of the preceding embodiments, wherein said paraxanthine is between 0.5% and 10% (w/w) of said composition.

118. The composition of any one of the preceding embodiments, wherein said paraxanthine is between 0.5% and 9% (w/w) of said composition.

119. The composition of any one of the preceding embodiments, wherein said paraxanthine is between 0.5% and 8% (w/w) of said composition.

120. The composition of any one of the preceding embodiments, wherein said paraxanthine is between 0.5% and 7% (w/w) of said composition.

121. The composition of any one of the preceding embodiments, wherein said paraxanthine is between 0.5% and 6% (w/w) of said composition.

122. The composition of any one of the preceding embodiments, wherein said paraxanthine is between 0.5% and 5% (w/w) of said composition.

123. The composition of any one of the preceding embodiments, wherein said paraxanthine is between 0.5% and 4% (w/w) of said composition.

124. The composition of any one of the preceding embodiments, wherein said paraxanthine is between 0.5% and 3% (w/w) of said composition.

125. The composition of any one of the preceding embodiments, wherein said paraxanthine is between 0.5% and 2% (w/w) of said composition.

126. The composition of any one of the preceding embodiments, wherein said paraxanthine is between 0.5% and 1.75% (w/w) of said composition.

127. The composition of any one of the preceding embodiments, wherein said paraxanthine is between 0.5% and 1.5% (w/w) of said composition.

128. The composition of any one of the preceding embodiments, wherein said paraxanthine is between 0.5% and 1.4% (w/w) of said composition.

129. The composition of any one of the preceding embodiments, wherein said paraxanthine is between 0.5% and 1.3% (w/w) of said composition.

130. The composition of any one of the preceding embodiments, wherein said paraxanthine is between 0.5% and 1.25% (w/w) of said composition.

131. The composition of any one of the preceding embodiments, wherein said paraxanthine is between 0.5% and 1.20% (w/w) of said composition.

132. The composition of any one of the preceding embodiments, wherein said paraxanthine is about 1.5% (w/w) of said composition.

133. The composition of any one of the preceding embodiments, wherein said paraxanthine is about 1.4% (w/w) of said composition.

134. The composition of any one of the preceding embodiments, wherein said paraxanthine is about 1.3% (w/w) of said composition.

135. The composition of any one of the preceding embodiments, wherein said paraxanthine is about 1.2% (w/w) of said composition.

136. The composition of any one of the preceding embodiments, wherein said paraxanthine is about 1.1% (w/w) of said composition.

137. The composition of any one of the preceding embodiments, wherein said paraxanthine is about 1.0% (w/w) of said composition.

138. The composition of any one of the preceding embodiments, wherein said paraxanthine is about 0.9% (w/w) of said composition.

139. The composition of any one of the preceding embodiments, wherein said paraxanthine is about 0.8% (w/w) of said composition.

140. The composition of any one of the preceding embodiments, wherein said paraxanthine is about 0.7% (w/w) of said composition.

141. The composition of any one of the preceding embodiments, wherein said paraxanthine is about 0.6% (w/w) of said composition.

142. The composition of any one of the preceding embodiments, wherein said paraxanthine is about 0.5% (w/w) of said composition.

143. The composition of any one of the preceding embodiments, wherein said paraxanthine is about 0.4% (w/w) of said composition.

144. The composition of any one of the preceding embodiments, wherein said paraxanthine is about 0.3% (w/w) of said composition.

145. The composition of any one of the preceding embodiments, wherein said paraxanthine is about 0.2% (w/w) of said composition.

146. The composition of any one of the preceding embodiments, wherein said paraxanthine is about 0.1% (w/w) of said composition.

147. The composition of any one of the preceding embodiments, wherein said paraxanthine is about 0.075% (w/w) of said composition.

148. The composition of any one of the preceding embodiments, wherein said paraxanthine is about 0.05% (w/w) of said composition.

149. The composition of any one of the preceding embodiments, wherein said paraxanthine is about 0.025% (w/w) of said composition.

150. The composition of any one of the preceding embodiments, wherein said paraxanthine is about 0.01% (w/w) of said composition.

151. The composition of any one of the preceding embodiments, wherein said paraxanthine is about 0.0075% (w/w) of said composition.

152. The composition of any one of the preceding embodiments, wherein said paraxanthine is about 0.005% (w/w) of said composition.

153. The composition of any one of the preceding embodiments, wherein said paraxanthine is about 0.1% (w/w) of said composition.

154. The composition of any one of the preceding embodiments, wherein said caffeine is less than about 2.5% (w/w) of said composition.

155. The composition of any one of the preceding embodiments, wherein said caffeine is less than about 2.25% (w/w) of said composition.

156. The composition of any one of the preceding embodiments, wherein said caffeine is less than about 2.0% (w/w) of said composition.

157. The composition of any one of the preceding embodiments, wherein said caffeine is less than about 1.75% (w/w) of said composition.

158. The composition of any one of the preceding embodiments, wherein said caffeine is less than about 1.5% (w/w) of said composition.

159. The composition of any one of the preceding embodiments, wherein said caffeine is less than about 1.25% (w/w) of said composition.

160. The composition of any one of the preceding embodiments, wherein said caffeine is less than about 1.0% (w/w) of said composition.

161. The composition of any one of the preceding embodiments, wherein said caffeine is less than about 0.9% (w/w) of said composition.

162. The composition of any one of the preceding embodiments, wherein said caffeine is less than about 0.8% (w/w) of said composition.

163. The composition of any one of the preceding embodiments, wherein said caffeine is less than about 0.7% (w/w) of said composition.

164. The composition of any one of the preceding embodiments, wherein said caffeine is less than about 0.6% (w/w) of said composition.

165. The composition of any one of the preceding embodiments, wherein said caffeine is less than about 0.5% (w/w) of said composition.

166. The composition of any one of the preceding embodiments, wherein said caffeine is less than about 0.3% (w/w) of said composition.

167. The composition of any one of the preceding embodiments, wherein said caffeine is less than about 0.2% (w/w) of said composition.

168. The composition of any one of the preceding embodiments, wherein said caffeine is less than about 0.1% (w/w) of said composition.

169. The composition of any one of the preceding embodiments, wherein said caffeine is between about 0.2% (w/w) and 0.8% (w/w) of said composition.

170. The composition of any one of the preceding embodiments, wherein said caffeine is between about 0.3% (w/w) and 0.7% (w/w) of said composition.

171. The composition of any one of the preceding embodiments, wherein said caffeine is between about 0.4% (w/w) and 0.6% (w/w) of said composition.

172. The composition of any one of the preceding embodiments, wherein said caffeine is between about 0.005% and 0.15% (w/w) of said composition.

173. The composition of any one of the preceding embodiments that is not a beverage, wherein the moisture is less than about 10% (w/w) of said composition.

174. The composition of any one of the preceding embodiments that is not a beverage, wherein the said moisture is less than about 9% (w/w) of said composition.

175. The composition of any one of the preceding embodiments that is not a beverage, wherein the moisture is less than about 8% (w/w) of said composition.

176. The composition of any one of the preceding embodiments that is not a beverage, wherein the moisture is less than about 7.5% (w/w) of said composition.

177. The composition of any one of the preceding embodiments that is not a beverage, wherein the moisture is less than about 7.0% (w/w) of said composition.

178. The composition of any one of the preceding embodiments that is not a beverage, wherein the moisture is less than about 6.5% (w/w) of said composition.

179. The composition of any one of the preceding embodiments that is not a beverage, wherein the moisture is less than about 5.5% (w/w) of said composition.

180. The composition of any one of the preceding embodiments that is not a beverage, wherein the moisture is less than about 5.0% (w/w) of said composition.

181. The composition of any one of the preceding embodiments that is not a beverage, wherein the moisture is less than about 4.5% (w/w) of said composition.

182. The composition of any one of the preceding embodiments that is not a beverage, wherein the moisture is less than about 4% (w/w) of said composition.

183. The composition of any one of the preceding embodiments that is not a beverage, wherein the moisture is less than about 3% (w/w) of said composition.

184. The composition of any one of the preceding embodiments that is not a beverage, wherein the moisture is less than about 2% (w/w) of said composition.

185. The composition of any one of the preceding embodiments that is not a beverage, wherein the moisture is less than about 1% (w/w) of said composition.

186. The composition of any of the preceding embodiments, wherein said composition has an Agtron scale score between 20 and 90.

187. The composition of any of the preceding embodiments, wherein the coffee, coffee bean or coffee beverage, if mentioned, is derived from the species *Coffea arabica*.

188. The composition of any of the preceding embodiments, wherein the coffee, coffee bean or coffee beverage, if mentioned, is derived from the species *Coffea robusta*.

189. The composition of any of the preceding embodiments, wherein the coffee, coffee bean or coffee beverage, if mentioned, is derived from the species *Coffea arabica*.

190. The composition of any of the preceding embodiments, wherein the coffee, coffee bean or coffee beverage, if mentioned, is derived from the species *Coffea robusta*.

191. The composition of any of the preceding embodiments, wherein the coffee, coffee bean or coffee beverage, if mentioned, is derived from the species Coffee *liberica*.

192. The composition of any of the preceding embodiments, wherein the coffee, coffee bean or coffee beverage, if mentioned, is derived from the species *Coffea charrieriana*

193. The composition of any of the preceding embodiments, wherein said paraxanthine coffee bean, if mentioned, is a whole bean.

194. The composition of any of the preceding embodiments, wherein said paraxanthine coffee bean, if mentioned, is a ground bean.

195. The composition of any of the preceding embodiments, wherein said paraxanthine is derived from a naturally occurring source.

196. The composition of any of the preceding embodiments, wherein said paraxanthine is produced synthetically.

197. The composition of any one of the preceding embodiments, wherein said paraxanthine is biologically derived.

198. The composition of any of the preceding embodiments, wherein said paraxanthine has a purity of greater than about 95% by weight.

199. The composition of any of the preceding embodiments, wherein said paraxanthine has a purity of greater than about 97.5% by weight.

200. The composition of any of the preceding embodiments, wherein said paraxanthine has a purity of greater than about 98% by weight.

201. The composition of any of the preceding embodiments, wherein said paraxanthine has a purity of greater than about 99% by weight.

202. The composition of any of the preceding embodiments, wherein said paraxanthine has a purity of greater than about 99.9% by weight.

203. A method of producing a composition of any one of the preceding embodiments, wherein the paraxanthine composition is a roasted, whole bean paraxanthine coffee bean, comprising the steps of:
   1) Infusing a green coffee bean with an infusion solvent and paraxanthine to produce a green solvated paraxanthine coffee bean;
   2) Drying the green solvated paraxanthine coffee bean to produce a green paraxanthine coffee bean; and,
   3) Roasting the green paraxanthine coffee bean to produce a whole bean paraxanthine coffee.

204. A method of producing a composition of any one of the preceding embodiments, wherein the paraxanthine composition is a roasted, ground paraxanthine coffee, comprising the steps of:
   1) Infusing a green coffee bean with an infusion solvent and paraxanthine to produce a green solvated paraxanthine coffee bean;
   2) Drying the green solvated paraxanthine coffee bean to produce a green paraxanthine coffee bean;
   3) Roasting the green paraxanthine coffee bean to produce a whole bean paraxanthine coffee; and
   4) grinding the whole bean paraxanthine coffee to produce a ground paraxanthine coffee.

205. The method of any one of the preceding method embodiments, wherein said infusion solvent comprises water.

206. The method of any one of the preceding method embodiments, wherein said infusion solvent comprises ethyl acetate.

207. The method of any one of the preceding method embodiments, wherein said infusion solvent comprises methylene chloride.

208. The method of any one of the preceding method embodiments, wherein said infusion solvent comprises ethanol.

209. The method of any one of the preceding method embodiments, wherein said infusion solvent comprises isopropanol.

210. The method of any one of the preceding method embodiments, wherein said infusing step is performed at a pH between 4 and 10.

211. The method of any one of the preceding method embodiments, wherein said infusing step is performed at a pH between 5 and 9.

212. The method of any one of the preceding method embodiments, wherein said infusing step is performed at a pH between 6 and 8.5.

213. The method of any one of the preceding method embodiments, wherein said infusing step is performed at a pH between 6 and 8.25.

214. The method of any one of the preceding method embodiments, wherein said infusing step is performed at a temperature between 4° C. and 95° C.

215. The method of any one of the preceding method embodiments, wherein said infusing step is performed at a temperature between 4° C. and 80° C.

216. The method of any one of the preceding method embodiments, wherein said infusing step is performed at a temperature between 4° C. and 70° C.

217. The method of any one of the preceding method embodiments, wherein said infusing step is performed at a temperature between 4° C. and 60° C.

218. The method of any one of the preceding method embodiments, wherein said infusing step is performed at a temperature between 4° C. and 50° C.

219. The method of any one of the preceding method embodiments, wherein said drying step is performed at atmospheric pressure.

220. The method of any one of the preceding method embodiments, wherein said drying step is performed under vacuum.

221. The method of any one of the preceding method embodiments, wherein said drying step is performed at a temperature between 4° C. and 150° C.

222. The method of any one of the preceding method embodiments, wherein said drying step is performed at a temperature between 4° C. and 100° C.

223. The method of any one of the preceding method embodiments, wherein said infusing step is performed at a temperature between 4° C. and 75° C.

224. The method of any one of the preceding method embodiments, wherein said infusing step is performed at a temperature between 4° C. and 50° C.

225. The method of any one of the preceding method embodiments, wherein said infusing step is performed at a temperature between 4° C. and 45° C.

226. The method of any one of the preceding method embodiments, wherein said infusing step is performed at a temperature between 4° C. and 40° C.

227. The method of any one of the preceding method embodiments, wherein said infusing step is performed at a temperature between 4° C. and 35° C.

228. The method of any one of the preceding method embodiments, wherein said infusing step is performed at a temperature between 4° C. and 30° C.

229. The method of any one of the preceding method embodiments, wherein said infusing step is performed at a temperature between 4° C. and 25° C.

EXAMPLES

Example 1: Preparation of Paraxanthine Coffees and Paraxanthine Coffee Beverages Coffee beans are decaffeinated by extracting out caffeine from the coffee beans into a water solution containing decaffeinated coffee extracts, to selectively remove caffeine from the coffee beans and leave desirable flavorants. The decaffeinated coffee beans thus obtained have a caffeine content of less than 0.1% w/w.

Paraxanthine is then added to the decaffeinated coffee beans by solid-solid grinding, paraxanthine absorption, or paraxanthine adsorption.

For solid-solid grinding, 3.75 g of solid paraxanthine is directly ground into 15 g of decaffeinated roasted coffee beans using a mortar and pestle, in a ratio of paraxanthine to coffee beans between 10% and 30% by weight to produce a paraxanthine coffee with 20% w/w paraxanthine. The resulting 20% w/w paraxanthine coffee is then used to produce a 1.5% w/w paraxanthine coffee by mixing 1 gram of the 20% w/w paraxanthine coffee with 12.33 g of decaffeinated coffee, thereby producing 13.33 gram of paraxanthine coffee comprising 1.5% w/w paraxanthine.

For addition of paraxanthine to decaffeinated coffee beans by absorption, green, unroasted decaffeinated coffee beans are soaked in a concentrated paraxanthine aqueous solution of 100 g/l paraxanthine containing green coffee extract, at a temperature of 100° C. to allow paraxanthine diffusion into the coffee beans until equilibrium is reached.

For addition of paraxanthine to coffee beans by adsorption, unroasted or roasted decaffeinated coffee beans are coated with 60 ml of 25 g/l paraxanthine solution in supercritical carbon dioxide on the outer surface of the beans, and the supercritical carbon dioxide is then allowed to evaporate, to produce 100 grams of paraxanthine coffee beans coated with a thin layer of paraxanthine.

The paraxanthine coffee thus produced has desirable flavor and texture and provides consumers with the desired alertness.

Example 2: Preparation of Paraxanthine Coffee by Solid-Solid Grinding

A paraxanthine coffee was prepared by solid-solid grinding of paraxanthine with decaffeinated coffee using 4.0 grams of >99% pure, synthetic paraxanthine and ground, roasted decaffeinated coffee beans produced by ethyl acetate extraction of caffeine.

First, a 10 gram sample of the ground decaffeinated coffee beans was set aside for purposes of measuring the residual caffeine content of the decaffeinated coffee as described below.

Second, 3.75 g of paraxanthine were ground with 15 g of roasted decaffeinated coffee using a mortar and pestle. The paraxanthine started as a white, crystalline powder and, following solid-solid grinding with the roasted decaffeinated coffee, developed a uniform, light coffee color. The resulting paraxanthine-decaffeinated coffee mixture ("Mixture 1") was approximately 18.75 grams. Mixture 1 was then thoroughly mixed with an additional 321.25 grams of decaffeinated coffee to generate a 340 g of paraxanthine coffee. The paraxanthine coffee had a uniform coffee color and texture indistinguishable from the initial roasted decaffeinated coffee.

Lastly, the caffeine and paraxanthine contents of both the starting, decaffeinated coffee and the final, paraxanthine coffee were quantified. 10 grams of the initial, roasted decaffeinated coffee or 10 grams of the final, paraxanthine coffee were placed in a glass french press and mixed with 700 grams of hot water (95° C.). The mixture was allowed to steep for a period of about 20 minutes to extract the caffeine and paraxanthine. Subsequently, the residual coffee solids were removed by filtration.

The caffeine and paraxanthine contents of the aqueous solution for each sample were then measured by high performance liquid chromatography (HPLC). HPLC analysis was performed on a HPLC device equipped with a C18 column (4.6×100 mm) and UV-VIS detector monitoring absorption at 272 nm. The column temperature was held at 40° C. and the mobile phase flow rate was held constant at 0.5 ml/min. Sample injection volumes were 5 µl. Mobile Phase A ("A") comprised 0.5% acetic acid in water and Mobile Phase B ("B") comprised methanol. The protocol consisted of 85% A and 15% B for 1 min, ramp up to 25% B at 7 min, and maintain until 10.5 min, and then ramp down to 15% B from 10.55 min to 12 min. Caffeine and paraxanthine concentrations were measured by comparison to standard curves prepared from 100-250 mg/l of both compounds; the retention time of caffeine and paraxanthine were 10.72 minutes and 7.14 minutes, respectively. The caffeine content in both the starting, decaffeinated coffee and the final, paraxanthine coffee was about 0.01% (w/w). The paraxanthine content of the starting, decaffeinated coffee and the paraxanthine coffee were below the limit of detection and 1.08% w/w, respectively.

These results indicated that a paraxanthine coffee comprising less than 0.1% w/w caffeine and about 1.1% (w/w) paraxanthine can be successfully prepared by the disclosed methods.

Example 3: Preparation of Green Coffee Extract

In various embodiments of the methods of the present disclosure, the infusion mixture of Step 1, infusing, comprises green coffee extract. This example describes production of a green coffee extract comprising less than 1% w/w caffeine.

First, 2.5 kg of green coffee beans comprising 0.01% w/w caffeine were mixed with 7.5 kg of water (i.e., a 3:1 ratio of water to green coffee beans). The mixture was heated to 85° C. and continuously mixed for a period of 4 hours. Subsequently, the green coffee beans were separated using a metal sieve to produce green coffee extract.

The paraxanthine and caffeine content of the green coffee extract was measured by high-performance liquid chromatography (HPLC). HPLC analysis was performed on a HPLC device equipped with a C18 column (3.5 µm, 4.6×100 mm) and UV-VIS detector monitoring absorption at 272 nm. The column temperature was held at 40° C. and the mobile phase flow rate was held constant at 0.5 ml/min. Sample injection volumes were 5 l. Mobile Phase A ("A") comprised 0.5% acetic acid in water and Mobile Phase B ("B") comprised methanol. The protocol consisted of 85% A and 15% B for 1 min, ramp up to 25% B at 7 min, and maintain until 10.5 min, and then ramp down to 15% B from 10.55 min to 12 min. Caffeine and paraxanthine contents (µg/g) were measured by comparison to standard curves prepared from 50-400 µg/g of each compound and mass fractions in the original coffee samples calculated.

The caffeine content of the green coffee extract was determined to be 0.27 mM; no paraxanthine was detectable in the green coffee extract. The green coffee extract is suitable for use as a component of infusion mixtures described herein.

Example 4: Preparation of Paraxanthine Coffee by Infusion Method

This example describes the preparation of whole bean and paraxanthine coffees derived from *Coffea arabica* and *Coffea robusta* species wherein said paraxanthine coffees have a paraxanthine content of between 0.1% to 5% w/w, a caffeine content of less than 2.5% w/w, a moisture content of less than 10% w/w, and an Agtron scale score between 20 and 90.

In this example, three different types of green coffee beans were used to generate paraxanthine coffee. Batch numbers 1 and 2 refer to green coffee beans derived from *Coffea arabica* wherein the initial caffeine contents were 0.01% and 0.61% w/w, respectively, and the initial moisture contents were 6.33% and 6.43% w/w, respectively. Batch 3 refers to green coffee beans derived from *Coffea robusta* wherein the initial caffeine content was 1.86% w/w and the initial moisture content was 7.73%. No paraxanthine was detectable in any of the green coffee beans.

In the first, infusing, step, the three batches of green coffee beans were individually infused with paraxanthine dissolved in water, the infusion solvent, to produce green solvated paraxanthine coffee beans. A stock solution of infusion solvent comprising paraxanthine was generated by mixing 18 grams of paraxanthine in 1 liter of water at 85° C.; the solution was then filtered to remove any residual, undissolved paraxanthine. The paraxanthine concentration in the stock solution was approximately 74 mM. Infusions were performed in 250-mL glass jars using 60 grams of green coffee beans and 120 grams of the stock infusion solution. The mixtures were incubated at 85° C. for 1 hour with periodic mixing. Subsequently, the green solvated paraxanthine coffee beans were separated using a colander, rinsed, and residual solvent removed from the surface of the beans. The mass of the infused beans was measured and compared to the mass of the original green coffee beans to determine the infusion solvent content. The moisture contents for batches 1, 2, and 3 were 45.1%, 46.9%, and 44.8%, respectively.

In the second, drying, step the green solvated paraxanthine coffee beans were incubated at 42.5° C. for 24 hours at atmospheric pressure. The infusion solvent content was then measured using a moisture analyzer (Forelibra; MA110) wherein a 4-5 g sample was heated to 120° C. and the loss in mass monitored over time; the analysis was stopped when the rate of mass loss decreased to below 1 mg in 30 seconds. The moisture content for batches 1, 2, and 3 were 4.29%, 7.49%, and 4.34%, respectively. Paraxanthine content was measured by HPLC per Example 3 following extraction of paraxanthine from the beans into hot water. The paraxanthine contents for batches 1, 2, and 3 were 0.95%, 0.50%, and 0.88% w/w, respectively. Thus, the drying step transformed the green solvated paraxanthine coffee beans into green paraxanthine coffee beans.

Next, 30-40 gram samples of the green paraxanthine coffee beans were roasted on an IKAWA Pro100. The temperature was increased from 138° C. to 211° C. over a total period of 6.25 to 6.5 minutes. Following roasting, the caffeine content, paraxanthine content, moisture content, and Agtron scale score were determined for each batch.

Caffeine and paraxanthine contents were determined as follows. The roasted beans were ground to a fine powder (<100 μm particle size), and then 5-6 g samples were added to 40-50 grams of 95° C. water in 50-mL centrifuge tubes and incubated for 1 hr. Subsequently, 1 mL samples of the aqueous phase were transferred to 2.0-mL centrifuge tubes equipped with 0.2-micron spin filters, centrifuged (7,000-x g, 2 min), and the flow-through analyzed by HPLC. The paraxanthine contents of batches 1, 2, and 3 were 1.21%, 1.11%, and 1.06% w/w, respectively, and the caffeine contents were 0.02%, 0.99%, and 1.49%, respectively.

The moisture content of the roasted beans was determined for 4-5 gram samples of ground, roasted paraxanthine coffee using a commercial moisture analyzer (Forelibra; MA110) as follows. The samples were incubated at 120° C. and the rate of mass loss monitored over time; the analysis was stopped when the rate of mass loss decreased to less than 1 mg in 30 seconds. Moisture contents were as follows for Batches 1, 2, and 3, respectively: 1.48%, 1.57%, and 1.45% w/w.

The color (Agtron scale score) of the roasted coffee beans was measured using a Dipper KN-201 per manufacturer's directions. The Agtron scale scores were as follows for Batches 1, 2, and 3, respectively: 57.9, 60.0, and 80.9.

In summary, this Example demonstrates the application of the methods of the present disclosure to produce the disclosed whole bean and ground paraxanthine coffees starting with green coffee beans derived from both *Coffea arabica* and *Coffea robusta* species with different initial caffeine contents. The example also provides three batches of paraxanthine coffee wherein each comprised between 0.1% to 5% w/w paraxanthine, less than 2.5% w/w caffeine, less than 10% w/w moisture content, and wherein the Agtron scale score was between 20 and 90.

Example 5: Use of Infusion Solvent Comprising Ethyl Acetate

In this example, the infusing step was performed using a 50:50 mix of ethyl acetate and water in the infusion step. The starting green coffee beans used in this example were *Coffea arabica* beans comprising 0.01% w/w caffeine and an initial moisture content of 6.33% w/w. No paraxanthine was detectable in the green coffee beans.

For the infusing step, 61 grams of green coffee beans was mixed with 60 grams of ethyl acetate, 60 grams of water, and 4.05 grams paraxanthine. The infusion mixture was incubated at 25° C. for 16 hours, the beans isolated, and residual solvent removed from the surface of the bean. The moisture content was 44.5% w/w.

The green solvated paraxanthine coffee beans were dried by incubated at room temperature and pressure for 48 hours. The moisture and paraxanthine contents after this step were 3.31% w/w and 0.4% w/w, respectively.

The green paraxanthine coffee beans were then roasted per Example 4 to produce a whole bean paraxanthine coffee. The moisture content of the roasted paraxanthine coffee beans was 2.56% w/w and the paraxanthine and caffeine contents were 0.51% and 0.03% w/w, respectively. The Agtron scale score was 58.1.

Thus, this example demonstrates a variation on the method of generating whole bean and ground paraxanthine coffee wherein ethyl acetate is used as a component of the infusion solvent.

Example 6: Varying Infusion Mixture pH

In this example, the infusing step was performed using water as the infusion solvent at pH values of between 3 and 10. The initial green coffee beans used in this example were identical to those used for Example 5.

The infusing step was performed as described in Example 4 with the exception that the pH was adjusted by addition of either HCl or NaOH (see Table 1 for infusing step pH values). The drying step, roasting step, and all analytical measurements were as described in Examples 4 and 5. Table 1 provides the caffeine, paraxanthine, and moisture contents of the roasted paraxanthine-infused beans as well as the Agtron scale scores.

In summary, this example demonstrates how varying the pH of the infusion mixture comprising paraxanthine can be useful for modifying the paraxanthine content of the disclosed whole bean and ground paraxanthine coffees.

TABLE 1

| Batch # | Infusing Step pH | Caffeine Content (% w/w) | Paraxanthine Content (% w/w) | Moisture Content (% w/w) | Agtron Color Score |
|---|---|---|---|---|---|
| 4 | 3.0 | 0.02% | 0.93% | 1.92% | 54.3 |
| 5 | 4.3 | 0.04% | 0.84% | 2.22% | 55.5 |
| 6 | 8.10 | 0.02% | 1.27% | 0.33% | 55.3 |
| 7 | 9.25 | 0.02% | 1.38% | 2.56% | 57.8 |
| 8 | 10.0 | 0.02% | 1.41% | 1.45% | 53.0 |

Example 7: Benefits of Paraxanthine Coffee

Ten individuals evaluated their experience following of consumption of paraxanthine coffee as compared to caffeinated coffee.

Two batches of ground coffee beans were produced. Batch B1 was ground paraxanthine coffee beans (derived from *Coffea arabica*) comprising about 1.2% (w/w) paraxanthine, less than 0.1% (w/w) caffeine, and less than 6% (w/w) moisture; Batch B1 was prepared as described in Example 2. Batch B2 was a conventional ground coffee bean that contained no detectable level of paraxanthine and approximately 1.1-1.3% (w/w) caffeine. Thus, B1 was a ground paraxanthine coffee bean of this disclosure and B2 was a conventional, caffeinated coffee that served as a control.

In week 1, the ten participants consumed paraxanthine coffee prepared at home from the ground paraxanthine coffee beans (batch B1). The participants consumed the paraxanthine coffee for 5 days and subsequently reported the number of days they experienced the following metrics: increased alertness, improved productivity, improved mood, jitteriness, anxiety, restlessness, irritability, and insomnia. In week 2, the participants consumed a conventional, caffeinated coffee prepared at home from the ground conventional coffee beans (batch B2). The participants consumed the conventional, caffeinated coffee for 5 days and reported the number of days they experienced increased alertness, improved productivity, improved mood, jitteriness, anxiety, restlessness, irritability, and insomnia. The survey was blinded and participants were not aware of which coffee was being consumed each week.

The total number of days the group of ten participants reported experiencing each metric for the ground paraxanthine coffee beans (batch B1) was as follows: increased alertness, 45 days; improved productivity, 42 days; elevated mood, 39 days; jitteriness, 2 days; anxiety, 2 days; restlessness, 6 days; irritability, 1 day; insomnia, 6 days.

The total number of days the group of ten participants reported experiencing each metric for the ground conventional coffee beans (batch B2) was as follows: increased alertness, 32 days; improved productivity, 23 days; elevated mood, 13 days; jitteriness, 22 days; anxiety, 18 days; restlessness, 20 days; irritability, 15 days; insomnia, 20 days.

Thus, participants reported more days feeling increased alertness, improved productivity, and improved mood after consuming paraxanthine coffee as compared to conventional, caffeinated coffee. Likewise, participants reported fewer days feeling jitteriness, anxiety, restlessness, irritability, and insomnia after consuming paraxanthine coffee as compared to conventional, caffeinated coffee.

In summary, this example demonstrates the benefits of paraxanthine coffee as compared to conventional coffee. Participants reported feeling more alert, improved productivity, and improved mood while simultaneously feeling less jittery, less anxious, less restless, less irritable, and experiencing less insomnia.

It should be recognized that illustrated embodiments are only examples of the disclosed products and methods and should not be considered a limitation on the scope of the invention. Rather, the scope of the invention is defined by the following claims. We therefore claim as our invention all that comes within the scope and spirit of these claims.

The invention claimed is:

1. A method of simultaneously decaffeinating coffee beans and infusing paraxanthine into the coffee beans, comprising:
    contacting coffee beans having a caffeine content of greater than 0.3% w/w with a solvent comprising between 1 g/L and 100 g/L paraxanthine.

2. The method of claim 1, wherein the method further comprises separating the coffee beans from the solvent to provide decaffeinated coffee beans, wherein the caffeine content of the decaffeinated coffee beans is less than 0.3% w/w.

3. The method of claim 1, wherein the caffeine content of the decaffeinated coffee beans is less than 0.25% w/w caffeine.

4. The method of claim 1, wherein the paraxanthine content of the decaffeinated coffee beans is between 0.5% w/w to 4.0% w/w.

5. The method of claim 2, wherein the paraxanthine content of the decaffeinated coffee beans is between 0.5% w/w to 4.0% w/w.

6. The method of claim 1, wherein the solvent comprises one or more fluids selected from the group consisting of water, ethyl acetate, methylene chloride, liquid carbon dioxide, acetone, benzyl alcohol, 1,3-butylene glycol, castor oil, citric acid esters, ethanol, glycerin, hexane, isopropanol, methanol, 2-butanone, and 1,2-propanediol.

7. The method of claim 5, wherein the solvent comprises one or more fluids selected from the group consisting of water, ethyl acetate, ethanol, methylene chloride, supercritical carbon dioxide, and isopropanol.

8. The method of claim 5, wherein the solvent comprises one or more fluids selected from the group consisting of water, ethyl acetate, and ethanol.

9. The method of claim 5, wherein the solvent consists of ethyl acetate, a mixture of ethyl acetate and ethanol, a mixture of water, ethyl acetate, and ethanol, or a mixture of ethyl acetate and water.

10. The method of claim 5, wherein the solvent consists of water.

11. The method of claim 1, wherein the method further comprises drying and roasting the coffee beans.

12. A method for preparing a decaffeinated, paraxanthine-containing, whole coffee bean composition comprising:
    contacting whole coffee beans comprising a caffeine content of greater than 0.3% w/w with a solvent comprising between 1 g/L and 100 g/L paraxanthine, wherein caffeine is extracted from the whole coffee beans into the solvent and paraxanthine from the solvent is absorbed by the whole coffee beans in a single step; and
    separating the whole coffee beans from the solvent to provide the composition, wherein the caffeine content of the whole coffee beans in the composition is reduced to less than 0.1% w/w and the paraxanthine content of the whole coffee beans in the composition is between 0.5% w/w to 4.0% w/w.

13. The method of claim 11, wherein the solvent comprises one or more fluids selected from the group consisting of water, ethyl acetate, methylene chloride, liquid carbon dioxide, acetone, benzyl alcohol, 1,3-butylene glycol, castor oil, citric acid esters, ethanol, glycerin, hexane, isopropanol, methanol, 2-butanone, and 1,2-propanediol.

14. The method of claim 12, wherein the solvent comprises one or more fluids selected from the group consisting of water, ethyl acetate, ethanol, methylene chloride, supercritical carbon dioxide, and isopropanol.

15. The method of claim 12, wherein the solvent comprises one or more fluids selected from the group consisting of water, ethyl acetate, and ethanol.

16. The method of claim 12, wherein the solvent consists of ethyl acetate, a mixture of ethyl acetate and ethanol, a mixture of water, ethyl acetate, and ethanol, or a mixture of ethyl acetate and water.

17. The method of claim 12, wherein the solvent consists of water.

18. A method according to claim 12, further comprising one or both of (i) drying of the paraxanthine-containing decaffeinated whole coffee beans, and (ii) roasting of the paraxanthine-containing decaffeinated whole coffee beans.

* * * * *